(12) United States Patent
Taylor et al.

(10) Patent No.: US 6,508,759 B1
(45) Date of Patent: *Jan. 21, 2003

(54) STEREOSCOPIC PERCUTANEOUS VISUALIZATION SYSTEM

(75) Inventors: Charles S. Taylor, San Francisco, CA (US); Brian S. Donlon, Palo Alto, CA (US); Timothy R. Machold, Moss Beach, CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/429,763

(22) Filed: Oct. 28, 1999

Related U.S. Application Data

(63) Continuation of application No. 08/612,810, filed on Mar. 11, 1996, now Pat. No. 5,957,832, which is a division of application No. 08/227,366, filed on Apr. 13, 1994, now Pat. No. 5,588,949, which is a continuation-in-part of application No. 08/135,387, filed on Oct. 8, 1993, now abandoned.

(51) Int. Cl.$^7$ .............................. A61B 1/00; A61B 1/313
(52) U.S. Cl. ..................... 600/168; 600/101; 600/102; 600/114; 600/172; 600/176; 359/381
(58) Field of Search .................. 600/101, 102, 600/114, 162, 111, 166, 165, 172, 168; 359/367, 368, 376, 377, 385, 398, 462, 381

(56) References Cited

U.S. PATENT DOCUMENTS

| | | | |
|---|---|---|---|
| 799,114 A | * | 9/1905 | Tracey |
| 1,848,788 A | * | 3/1932 | Loeck |
| 2,637,317 A | * | 5/1953 | Martin |
| 3,417,746 A | * | 12/1968 | Moore et al. |
| 3,630,002 A | * | 12/1971 | Herbert |
| 3,664,330 A | * | 5/1972 | Deutsch ............ 385/902 |
| 3,685,509 A | * | 8/1972 | Bentall |

(List continued on next page.)

FOREIGN PATENT DOCUMENTS

| | | | |
|---|---|---|---|
| AT | 78668 | * | 9/1917 |
| DE | 289924 A5 | * | 5/1991 |
| EP | 0479565 | * | 4/1992 |
| EP | 0556056 | * | 8/1993 |
| GB | 2255651 | * | 11/1992 |
| WO | 92/10969 | * | 7/1992 |
| WO | 93/20741 | * | 10/1993 |

OTHER PUBLICATIONS

Hoerenz, P. "The Operating Microscope I. Optical Rinciples, Illumination systems and Support Systems", J. Microsurgery, Mar./Apr. 1980 1:364–369.*

Hoerenz, P. "The Operating Microscope II. Individual Parts, Handling Assembly, Focusing and Balancing", J. Microsurgery, May/Jun. 1980 1:419–427.*

Hoerenz, P. "The Operating Microscope III. Accessories", J. Microsurgery, Sep. 1980, 2:22–26.*

(List continued on next page.)

*Primary Examiner*—John P. Leubecker

(57) ABSTRACT

A surgical microscope comprising a microscope body, lens means attached to the microscope body for magnifying an object image, an eyepiece attached to the microscope body for viewing the magnified object image, and coupling means attached to the microscope body for retaining a supplementary lens in optical alignment with the lens means, the coupling means being configured for introducing the supplementary lens through a percutaneous penetration into a body cavity, wherein the eyepiece and the lens means are configured to facilitate stereoscopic viewing. In a variation of the surgical microscope, a plurality of binocular eyepieces are attached to the microscope body to allow multiple persons to contemporaneously view the magnified object image.

7 Claims, 15 Drawing Sheets

U.S. PATENT DOCUMENTS

| | | | |
|---|---|---|---|
| 3,796,220 A | * 3/1974 | Bredemeier | 359/377 |
| 3,817,251 A | * 6/1974 | Hasson | |
| 3,870,036 A | * 3/1975 | Fiore | |
| 3,870,037 A | * 3/1975 | Cadariu et al. | 600/189 |
| 3,941,121 A | * 3/1976 | Olinger et al. | 600/167 |
| 3,994,287 A | * 11/1976 | Turp et al. | |
| 4,061,135 A | * 12/1977 | Widran et al. | |
| 4,167,302 A | * 9/1979 | Karasawa | 359/377 |
| 4,341,435 A | * 7/1982 | Lang et al. | |
| 4,350,147 A | * 9/1982 | Samine | |
| 4,364,629 A | * 12/1982 | Lang et al. | 600/162 |
| 4,525,042 A | * 6/1985 | Muchel | |
| 4,579,009 A | * 4/1986 | Carmichael et al. | |
| 4,605,287 A | * 8/1986 | Lang et al. | |
| 4,615,332 A | * 10/1986 | Buess et al. | |
| 4,786,161 A | * 11/1988 | Muller et al. | |
| 4,860,731 A | * 8/1989 | Matsura | |
| 4,877,016 A | * 10/1989 | Kantor et al. | |
| 4,973,321 A | * 11/1990 | Michelson | |
| 4,974,951 A | * 12/1990 | Sander et al. | |
| 4,987,471 A | * 1/1991 | Quinn et al. | |
| 4,997,419 A | * 3/1991 | Lakatos et al. | |
| 4,998,810 A | * 3/1991 | Sander et al. | |
| 5,039,198 A | * 8/1991 | VanBeek | |
| 5,112,308 A | * 5/1992 | Olsen et al. | |
| 5,158,543 A | * 10/1992 | Lazarus | |
| 5,169,387 A | * 12/1992 | Kronner | |
| 5,173,803 A | * 12/1992 | Heller | |
| 5,176,649 A | * 1/1993 | Wakabayashi | |
| 5,201,742 A | * 4/1993 | Hasson | |
| 5,213,093 A | * 5/1993 | Swindle | |
| 5,221,281 A | * 6/1993 | Klicek | |
| 5,271,592 A | * 12/1993 | Ludwig | |
| 5,282,085 A | * 1/1994 | Volkert et al. | |
| 5,295,477 A | * 3/1994 | Janfaza | 600/166 |
| 5,313,934 A | * 5/1994 | Wita et al. | |
| 5,321,447 A | * 6/1994 | Sander et al. | 359/381 |
| 5,330,501 A | * 7/1994 | Tovey et al. | |
| 5,339,800 A | * 8/1994 | Wita et al. | |
| 5,386,817 A | * 2/1995 | Jones | |
| 5,402,771 A | * 4/1995 | Pilling | |
| 5,452,733 A | * 9/1995 | Sterman | |
| 5,467,762 A | * 11/1995 | Sauer et al. | |
| 5,489,288 A | * 2/1996 | Buelna | |

OTHER PUBLICATIONS

Hoerenz, P. "The Operating Microscope IV. CDocumentation" J. Microsurgery, Dec. 1980, 2:126–139.*

Hoerenz, P. "The Operating Microscope V. Maintenance and Cleaning"—J. Microsurgery, Mar. 1981, 2:179–182.*

* cited by examiner

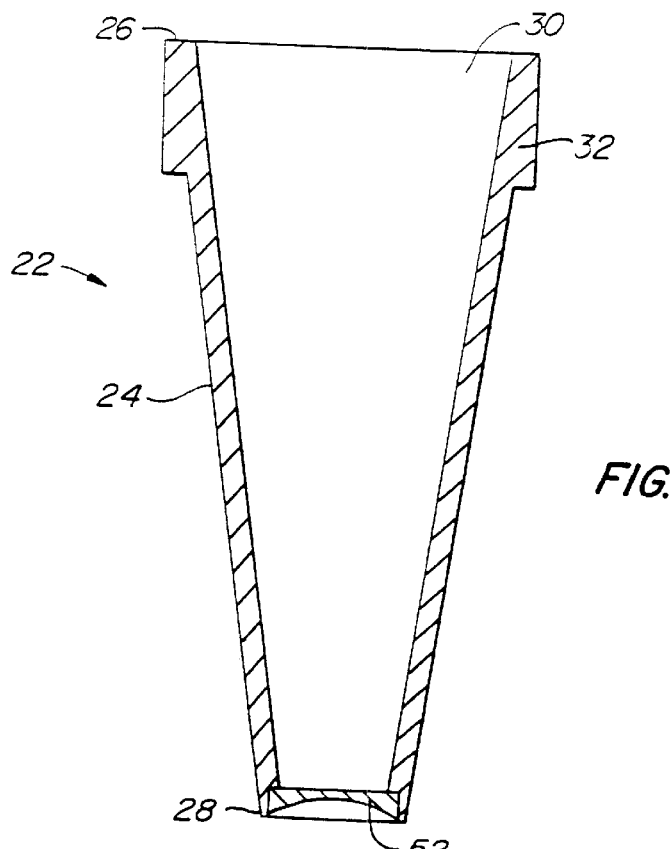
FIG. 3.
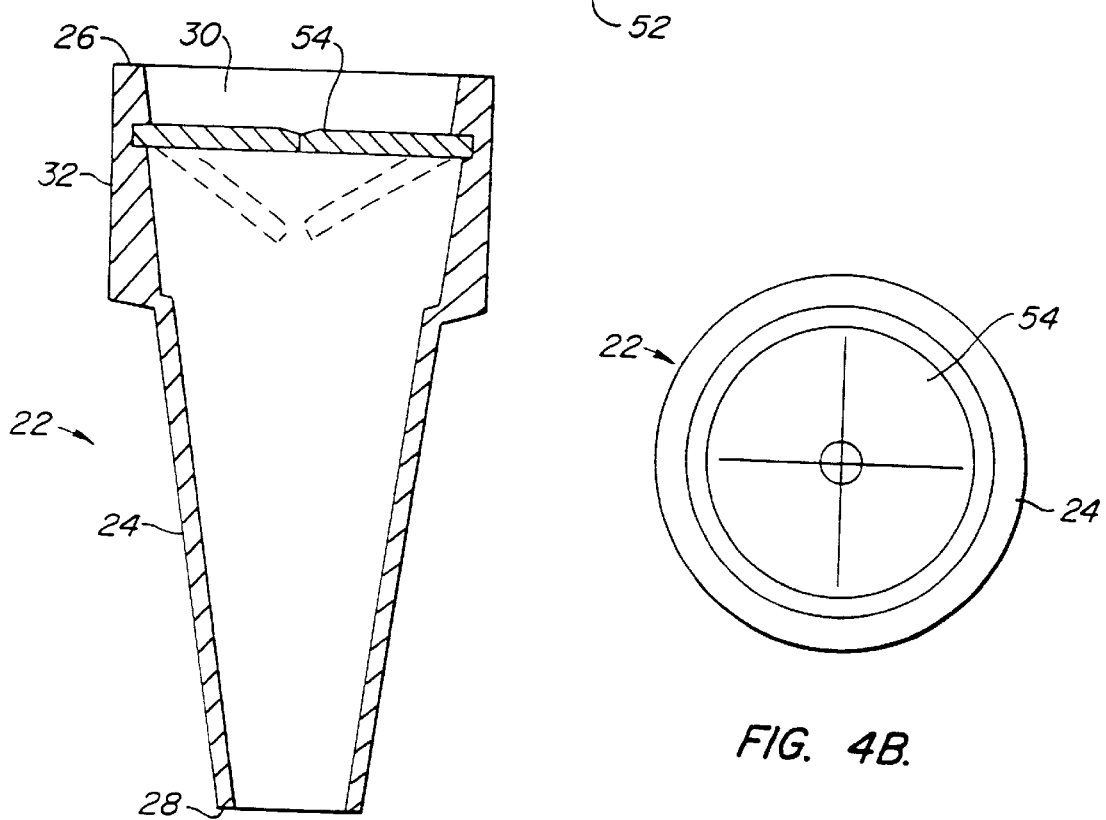
FIG. 4A.
FIG. 4B.

STEREOSCOPIC PERCUTANEOUS VISUALIZATION SYSTEM

CROSS-REFERENCE TO RELATED APPLICATION

This is a continuation of U.S. patent application Ser. No. 08/612,810 filed on Mar. 11, 1996, now issued as U.S. Pat. No. 5,957,832, which is a division of application Ser. No. 08/227,366, filed Apr. 13, 1994, now issued as U.S. Pat. No. 5,588,949, which is a continuation-in-part of U.S. patent application Ser. No. 08/135,387, filed Oct. 8, 1993, now abandoned, the complete disclosures of which are incorporated herein by reference.

FIELD OF THE INVENTION

This invention relates generally to surgical instruments for use in minimally-invasive surgical procedures such as endoscopy, thoracoscopy, laparoscopy, pelviscopy, and arthroscopy. More specifically, the invention relates to percutaneous visualization systems for use in such minimally-invasive surgical procedures.

BACKGROUND OF THE INVENTION

In minimally-invasive surgical techniques such as endoscopy, thoracoscopy, laparoscopy, pelviscopy, arthroscopy, and the like, elongated instruments are introduced into the body through small incisions or percutaneous cannulae to perform surgical procedures at an internal site, obviating the need for the large incisions characteristic of conventional, open surgical techniques. Visualization is facilitated by the use of specialized devices known as endoscopes, laparoscopes, pelviscopes, thoracoscopes, or arthroscopes, which typically consist of a rigid, elongated tube containing a lens system and, at the proximal end of the tube, an eyepiece or camera mount. The distal end of the tube is introduced into the body through an incision or cannula, and, by looking through the eyepiece, a surgeon may observe the interior of a body cavity. In addition, a small video camera may be attached to the camera mount and connected to a video monitor to provide a video image of the procedure. Usually, such visualization devices further include a light source at the distal end of the tube for illuminating the interior of the body cavity.

As the complexity of the procedures that can be performed by means of minimally-invasive techniques has increased, so has the demand for higher quality visualization systems to facilitate such procedures. For example, in commonly-assigned co-pending application Ser. No. 08/023,778, filed Feb. 22, 1993, the complete disclosure of which is incorporated herein by reference, new techniques are disclosed for performing coronary artery bypass grafting and other thoracic surgical procedures using minimally-invasive techniques. Coronary artery bypass grafting involves the use of microsurgical techniques to create an anastomosis, usually by suturing, between a coronary artery and either an existing artery such as the mammary artery, or a natural or synthetic arterial shunt connected to an upstream arterial blood source. As described in the forementioned patent application, long-handled microsurgical tools may be introduced through small incisions or cannulae positioned in the intercostal spaces of the rib cage to perform the anastomosis. Such procedures may take a team of surgeons up to several hours to complete. These intricate procedures therefore demand a visualization system that produces an extremely high-quality image of very small surgical sites, and that allows multiple surgeons to simultaneously view a surgical site comfortably over long periods of time.

While many of the visualization devices in current use have proven to be effective for use in certain minimally-invasive surgical procedures, such devices are frequently inadequate for the performance of complex microsurgical procedures such as coronary artery bypass grafting. For example, if just an eyepiece is used on an endoscope, only one person can look through the device at any one time, requiring an individual scope introduced through a separate incision or cannula for each person assisting in or observing the procedure. Further problematic is the difficulty in maintaining the eyepiece in alignment with the surgeon's eye for continual visualization while manipulating the instruments necessary to perform the procedure. Additionally, because these visualization devices are typically monoscopic, they have poor resolution of depth of field in comparison to a person's binocular, stereoscopic vision using both eyes.

By mounting a video camera on such visualization devices, more than one person may observe a procedure by watching a video monitor, without the need for additional incisions into the body cavity. However, the miniature video cameras in current use frequently produce sub-optimal image quality in comparison to direct vision through the scope. Further, indirect visualization by means of a video monitor rather than by direct sight is somewhat disorienting, and requires significant training and practice to develop the hand-eye coordination necessary to adeptly perform surgery. Additionally, where multiple surgeons are working in the surgical site under video imaging by a single scope, the video image can be correctly oriented relative to only one of the surgeons at any time. Other surgeons must adjust their actions to compensate for an inverted or otherwise misoriented image. Moreover, because most scopes, video electronics, and video displays in current use are monoscopic, video visualization also fails to provide the depth perception of normal stereoscopic vision.

What is needed, therefore, is a percutaneous visualization system for use in minimally-invasive surgical procedures that facilitates direct, stereoscopic visualization of a body cavity through a small incision or cannula. The visualization system should facilitate hand-eye coordination that is close or equal to that of open surgical procedures. Preferably, the visualization system will have the capability for wide-angle visualization as well as magnification to facilitate the performance of complex microsurgical procedures. Further, the visualization system should allow multiple surgeons to simultaneously view the same surgical site with comfort for long periods of time. The visualization system will preferably be configured for introduction through intercostal spaces of the rib cage for thoracoscopic procedures, but should be useful in any of a variety of minimally-invasive procedures, including laparoscopy, pelviscopy, arthroscopy and the like.

SUMMARY OF THE INVENTION

The invention provides a percutaneous visualization system and method that facilitate direct, stereoscopic visualization of a body cavity. The visualization system has both wide angle and magnification capabilities and produces extremely high image quality, thereby facilitating the performance of intricate microsurgical procedures using minimally-invasive techniques. Using the system and method of the invention, multiple surgeons may simultaneously view a surgical site comfortably for extended periods. The visualization system also allows various lenses to be easily interchanged or combined to optimize focal length and field of view. The system may further include a light source to illuminate the body cavity, as well as a passage for introduction of instruments into the body cavity. The system is particularly well-adapted for use in thoracoscopic procedures by positioning in intercostal spaces of the rib cage, but is also useful in endoscopic, laparoscopic, pelviscopic, arthroscopic, and other minimally-invasive procedures.

The visualization system of the invention includes a tubular cannula suitable for percutaneous introduction into a body cavity such as the thorax, abdomen, pelvis, cranium, or joint cavity. The cannula has an optical passage extending from its proximal end to its distal end that is configured to allow stereoscopic visualization of the body cavity. In a preferred embodiment, at least a portion of the optical passage is tapered toward the distal end at a taper angle selected to facilitate stereoscopic visualization of the body cavity through the optical passage. Usually, the taper angle of the optical passage will be at least 5° and less than 45°, and preferably between 5° and 20°.

In one embodiment, the optical passage is open from the proximal end to the distal end to allow surgical instruments, sutures, prostheses, tissue, light or light sources, visualization devices, and the like, to pass through the optical passage into or out of the body cavity. Alternatively, the cannula may include lens means mounted in the optical passage. The lens means preferably comprises a wide-angle lens system, such as a negative focal length lens, and may be permanently fixed or removably mounted in the optical passage. Such a lens means facilitates viewing a field within the body cavity which is substantially larger than the penetration through which the cannula is introduced—that is, substantially larger than the transverse cross-sectional area of the cannula itself. In a preferred embodiment, the lens means is mounted in a sleeve which is configured to be removably positioned in the optical passage. Where the optical passage is tapered, the sleeve is correspondingly tapered so as to nest within the cannula. In this way, the user may look directly through the optical passage in the cannula into the body cavity, or position a sleeve with wide-angle lens in the cannula to widen the field of view. Multiple sleeves with various lenses may be interchanged as the user desires.

The visualization system may further include magnification means that is optically alignable with the optical passage in the cannula. The magnification means preferably comprises a stereo-microscope positionable in alignment with the optical passage proximal to the cannula's proximal end. In a preferred embodiment, the stereo-microscope has a plurality of binocular eyepieces to allow multiple persons to view the surgical site simultaneously through the optical passage in the cannula. The use of a high-power stereo-microscope produces extremely high image quality at selectable magnification, thereby facilitating visualization of intricate microsurgical procedures. Alternatively, the magnification means may comprise binocular surgical telescopes, or "loupes," worn on the head of the user, much like eyeglasses with magnifying lenses.

The cannula is preferably configured for percutaneous introduction through an intercostal space in the rib cage into the thoracic cavity. The cannula may also be introduced into the abdominal cavity or into the pelvis. To facilitate introduction, the visualization system may further include an obturator or trocar that is positionable in the optical passage in the cannula. The obturator may have a sharpened or rounded tip that extends distally from the distal end of the cannula to penetrate tissue. Once the cannula has been positioned with its distal end in the body cavity, the obturator is removed.

The system may further include means for maintaining the cannula in a particular position or orientation relative to the patient's body. In a preferred embodiment, the means for maintaining the position of the cannula comprises a support structure that is fixed to the operating table supporting the patient, and a pivotable clamp attached to the support structure which may be clamped to the visualization cannula. In this way, the cannula may be positioned as desired and locked in place with the clamp. Alternatively, the cannula may be secured to the body of the patient, to the surgical drapes, to the surgical microscope, or to other supporting structures.

In a particularly preferred embodiment, the cannula of the invention is coupled directly to the microscope, thereby maintaining alignment between the two and securing the cannula in position. To facilitate interchanging lenses without decoupling the cannula from the microscope, an aperture may be provided in a side of the cannula in communication with the optical passage to allow lenses to be interchanged through the aperture. Alternatively, the sleeve which holds the lens means may be coupled to the microscope, the cannula remaining separate so that it may be positioned in the patient's body independently of the microscope and the sleeve. A means of coupling is preferably used which allows adjustment of the position of the cannula relative to the microscope along the optical axis of the microscope. This facilitates adjustment of the distance between the microscope objective and the lens means in the cannula to obtain proper focus at a desired distance when used with microscopes having a fixed focal length objective lens. In use, the cannula is usually positioned in the patient's body before coupling it to the microscope, and proper orientation of the cannula is obtained by direct visualization of the body cavity through the optical passage. With the cannula in position, the microscope is aligned with the cannula and the two are coupled together. Because the cannula enters into the body cavity and may come into direct contact with tissue within the body cavity, it is adapted for easy removal from the microscope for sterilization or disposal after use.

In addition, the visualization system may include means for illuminating the body cavity. The illuminating means may comprise a light source which is independent of the cannula, but, in a preferred embodiment, comprises a plurality of optical fibers fixed to the cannula and extending from its proximal end to its distal end. At the proximal end, the optical fibers may be connected to a light source so as to transmit light into the body cavity.

In a further preferred embodiment, the cannula of the invention includes means for directing a fluid onto a surface of a lens positioned in the passage of the cannula, for purposes such as removing debris or defogging the lens. The fluid directing means may comprise, for example, a lumen extending through the cannula body, a connector at the proximal end in communication with the lumen for connection to a fluid delivery source, and an opening at the distal end in communication with the lumen for directing the fluid onto the surface of the lens. The fluid may comprise a liquid such a saline solution for debris removal and/or irrigation, or a gas such as carbon dioxide for defogging or dehumidifying the lens.

The system and method of the invention offer significant advantages over previous visualization devices for use in minimally-invasive surgery. The invention provides the high image quality, natural hand-eye coordination and correct image orientation of direct vision, while allowing multiple persons to view the surgical site simultaneously. Visualization is further enhanced by the stereoscopic capability of the invention, which greatly improves depth perception. Moreover, the invention allows the use of high-power stereo microscopes with selectable magnification to produce an exceedingly high-quality image, making the invention particularly well-adapted for visualization of microsurgical procedures. Further advantages of the invention include the ability to interchange lenses easily, the capability for wide-angle viewing, as well as the ability to introduce or withdraw surgical instruments, body tissue, or prostheses into or out of the body cavity without the need for additional incisions.

A further understanding of the nature and advantages of the invention may be realized by reference to the remaining portions of the specification and the drawings.

BRIEF DESCRIPTION OF THE DRAWINGS

FIG. 3 is a front cross-sectional view of an alternative embodiment of the percutaneous visualization system of the invention.

FIG. 4A is front cross-sectional view of a second alternative embodiment of the percutaneous visualization system of the invention.

FIG. 4B is a top view of the percutaneous visualization system of FIG. 4A.

DETAILED DESCRIPTION OF SPECIFIC EMBODIMENTS

Figure 1:
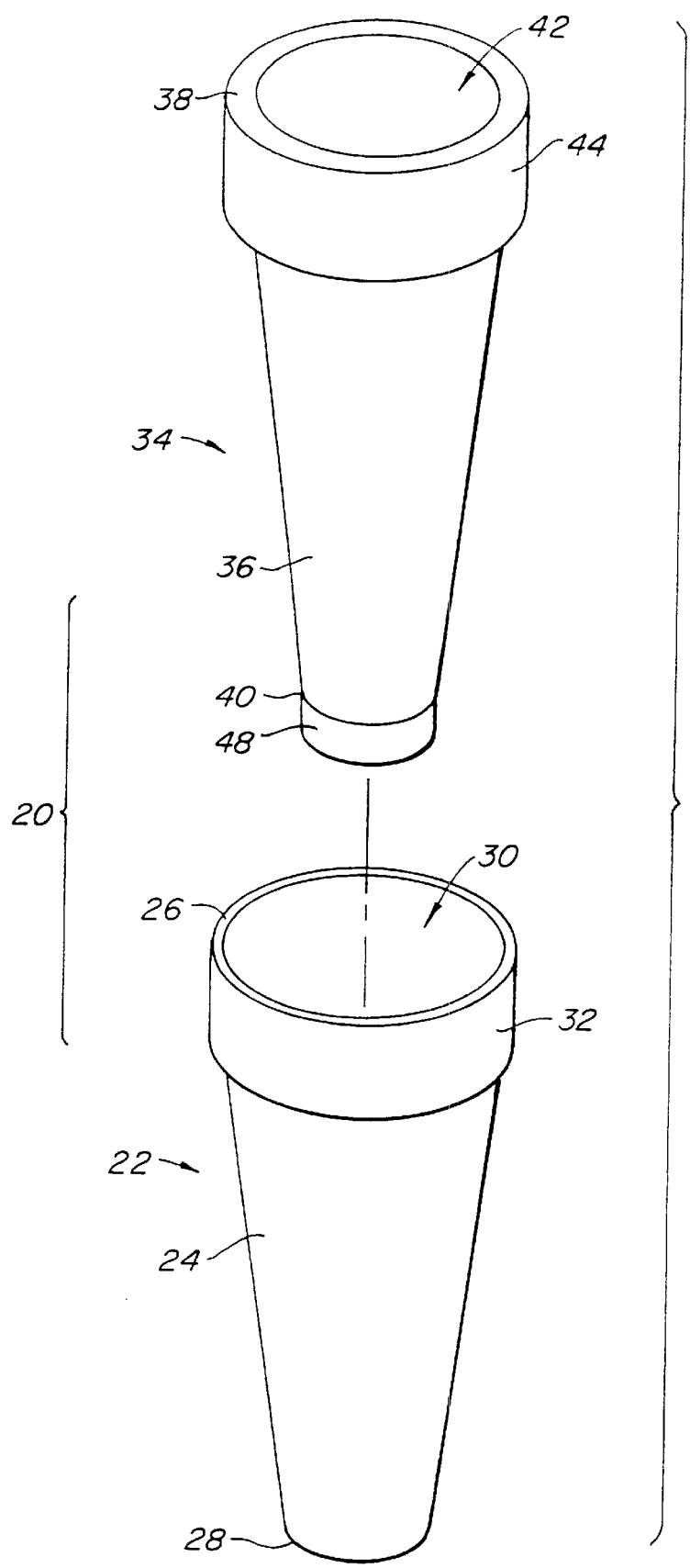
FIG. 1 is a perspective view of a percutaneous visualization system constructed in accordance with the principles of the present invention.

This invention is directed to a percutaneous visualization system for use in minimally-invasive surgical procedures, and particularly, for use in microsurgical procedures in which an extremely high-quality image of the surgical site is critical for success.

The invention will find use in a variety of endoscopic, thoracoscopic, laparoscopic, pelviscopic, arthroscopic, and other minimally-invasive procedures. The invention is particularly well-adapted, however, to facilitate visualization within the thoracic cavity during thoracoscopic surgery of the heart, lungs, thoracic vessels, and other thoracic contents. For example, the visualization system of the invention may be used in conjunction with the performance of thoracoscopic coronary artery bypass grafting (CABG) using the methods described in co-pending application Ser. No. 08/023,778, the disclosure of which has been incorporated herein by reference. As described in that application, coronary artery bypass grafting may be performed by means of microsurgical instruments introduced through percutaneous cannulae positioned in the chest wall in intercostal spaces of the rib cage. Microsurgical techniques are used to create an anastomosis, usually by suturing, between a coronary artery and either an existing artery such as the mammary artery, or a natural or synthetic arterial shunt connected to an upstream arterial blood source.

A major part of the thoracoscopic CABG procedure is performed on or near the surface of the heart where the coronary arteries are located. This area lies in the range of about two to ten centimeters below the interior surface of the chest wall and is surrounded by the rib cage, eliminating the need for fluid distension, which is required in laparoscopy, pelviscopy, arthroscopy, and the like. Thus, thoracoscopic CABG and other similar procedures present a unique set of considerations for visualization. First, from the interior of the chest wall, there is a relatively unobstructed view of the heart and other vessels in the thoracic cavity, in contrast to laparoscopy or pelviscopy, in which various organs and vessels will frequently lie between the abdominal wall and the surgical site. Second, in thoracoscopic CABG procedures, the surgical site to be visualized is relatively close to the chest wall, in comparison to many common laparoscopic surgical procedures, where the surgical site may be 10 to 30 cm from the point of entry through the abdominal wall. Third, because there is no need for fluid distension in thoracoscopic procedures, visualization devices need not be adapted to prevent fluid leakage from the body cavity. Finally, the microsurgical techniques used to perform procedures such as CABG require an extremely high-quality, stereoscopic image of the surgical site with good depth perception, and usually demand the ability to view the site at wide-angle as well as magnification. This invention responds to the need for a visualization system adapted for use under these unique conditions.

Figure 2:
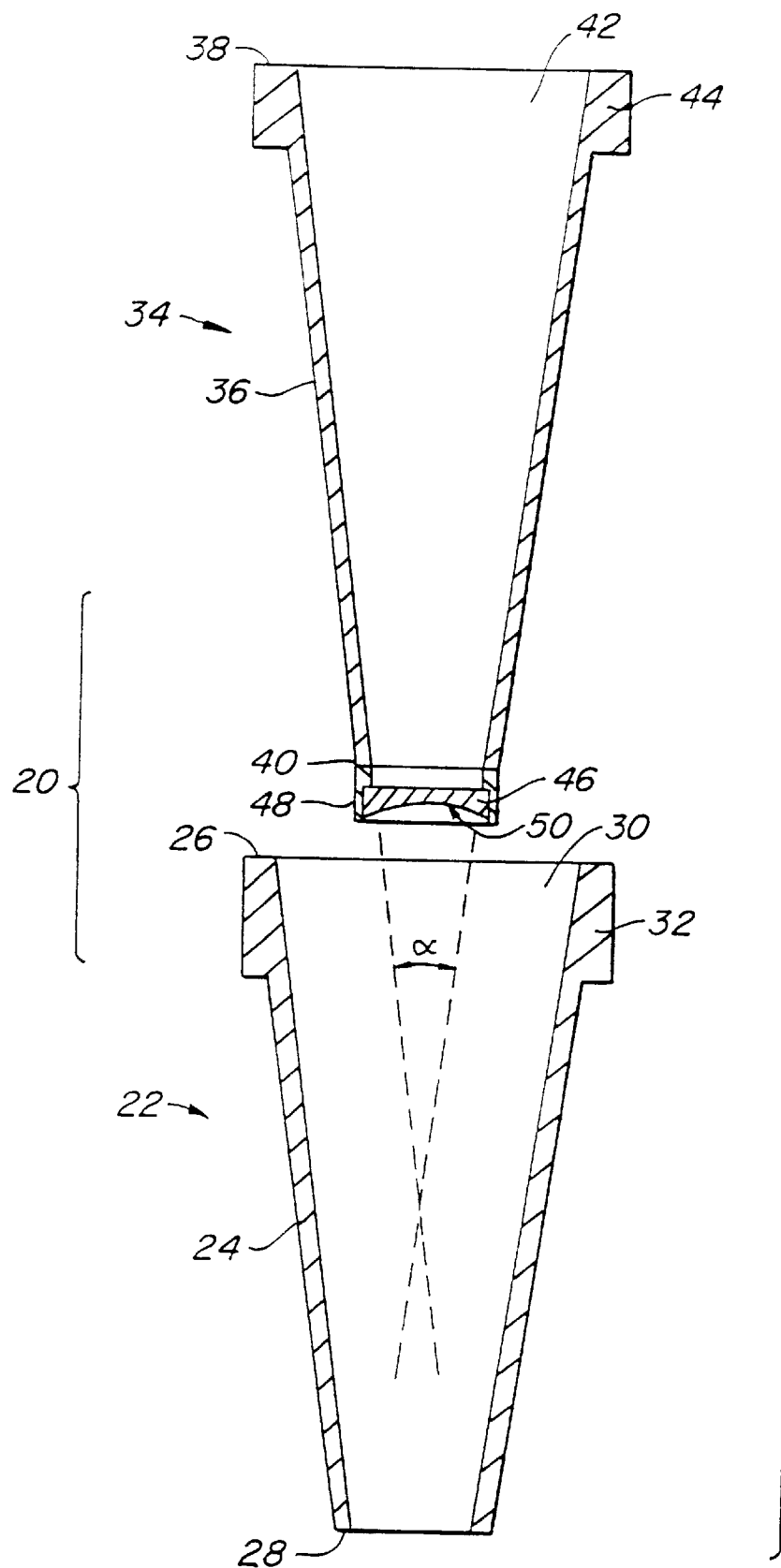
FIG. 2 is a front cross-sectional view of the percutaneous visualization system of FIG. 1.

A first embodiment of the visualization system of the invention is illustrated in FIGS. 1 and 2. Visualization system 20 includes a cannula 22 comprising a tubular cannula body 24 having a proximal end 26 and a distal end 28. A first passage 30 extends within cannula body 24 from proximal end 26 to distal end 28. In this embodiment, first passage 30 is open and unobstructed through the entire length of cannula body 24. Further, first passage 30 is tapered toward distal end 28 at a taper angle selected to allow stereoscopic visualization through cannula body 24, as described more fully below. The exterior of cannula body 24 may also be tapered as illustrated, so as to minimize the profile of the cannula and to facilitate percutaneous introduction into a body cavity. Usually, the exterior taper of cannula body 24 will be the same as the taper angle of first passage 30. A rim 32 may be provided about the exterior of cannula body 24 near proximal end 26, to allow for manual handling or attachment to holding or aligning devices.

Visualization system 20 further includes, in a preferred embodiment, a sleeve 34 comprising a tubular sleeve body 36 having a proximal end 38 and a distal end 40. An optical passage 42 extends between proximal end 38 and distal end 40. Optical passage 42 is tapered at a taper angle selected to allow stereoscopic visualization of a body cavity, as described more fully below. The exterior of sleeve body 36 is configured to allow sleeve 34 to be positioned within first passage 30 of cannula 22, and usually has a taper corresponding to that of first passage 30 so as to nest therein. Sleeve body 36 may also have a rim 44 at its proximal end 38 which seats against rim 32 of cannula 22.

The term "tubular" as used herein to describe cannula body 24 and sleeve body 36 is intended to encompass various cross-sectional shapes, including round, oval, rectangular, and the like. Further, cannula body 24 and/or sleeve body 36 may not have a continuous, solid wall, but instead may have longitudinal or circumferential slots or holes, or may have a cage or mesh structure with sufficient rigidity to maintain the shape and patency of first passage 30 and/or optical passage 42 when positioned in the wall of a body cavity.

Cannula body 24 and sleeve body 36 may be constructed of various materials, including metals such as stainless steel or plastics such as polycarbonate, or ABS. The length and transverse dimensions of cannula body 24 and sleeve body 36 may vary according to the procedure and patient for which they are adapted. In thoracoscopic procedures, cannula body 24 will usually have a length between about 5 cm and 15 cm, and a diameter at distal end 28 as small as 3 mm and no larger than about 20 mm in order to be positionable within an intercostal space of the rib cage. The diameter at proximal end 26 will depend upon the external taper (if any) of cannula body 24, and will preferably be about 10 mm to 50 mm.

In a preferred embodiment, a wide-angle lens system is mounted within or in optical alignment with optical passage 42 of sleeve 34. As shown in FIG. 2, in an exemplary embodiment, a lens 46 is mounted in alignment with optical passage 42 at or near distal end 40 of sleeve body 36. Lens 46 may be mounted directly within optical passage 42, or within a tubular lens mount 48 fixed to distal end 40 of the sleeve, as illustrated. In a preferred embodiment, lens 46 is a negative-focal length lens, having at least one concave surface 50. The focal length of lens 46 will be dictated by a number of considerations, including the distance of the site to be visualized from lens 46, and the size of the field desired. Focal lengths in the range of −6 to −12 mm, for example, are frequently useful to facilitate visualization of a coronary anastomosis procedure during closed-chest coronary artery bypass grafting. Such lenses are commercially available from Melles Griot of Irvine, Calif., Edmund Scientific Co. of Barrington, N.J., or Control Optics of Baldwin Park, Calif. Various lens configurations and lens combinations may be used to provide either wide-angle or magnification capabilities. In this way, multiple sleeves may be equipped with various types of lenses, and the sleeves interchanged in first passage 30 of cannula 22 according to the visualization capability desired.

As mentioned above, optical passage 42 and first passage 30 are preferably configured to allow stereoscopic vision into a body cavity. The term "stereoscopic vision" as used herein is intended to refer to the ability to see an object from two different angles. This is normally accomplished by a person simply looking at an object with his or her two eyes which, because they are slightly separated, provide two different angles of sight. Stereoscopic vision, as opposed to monoscopic vision, provides the ability to perceive depth in the object or objects visualized. In complex microsurgical procedures, such depth perception can be of great advantage.

In order to provide for stereoscopic vision, optical passage 42 and first passage 30 are preferably tapered at a taper angle a selected such that when sleeve 34 and cannula 22 are positioned in a patient with distal end 28 of the cannula within a body cavity, the user can look with both eyes through optical passage 42 from a comfortable position over the patient and see the surgical site. Taper angle a will therefore depend on a number of factors, including the location of the surgical site, the height of the user's eyes with respect to the patient, the length and diameter of cannula 22 and sleeve 34, and the type of lens (if any) in optical passage 42. Where the visualization system is configured for use in thoracoscopic procedures such as CABG, taper angle a will usually be at least 5°, and preferably between 5° and 30°, where cannula 22 and sleeve 34 each have a length between about 5 cm and 15 cm. Alternatively, optical passage 42 and first passage 30 may have a very slight taper or no taper at all, but will have an inner diameter which is large enough and a length which is short enough to allow stereoscopic vision into the body cavity. If magnification means such as a stereo-microscope or surgical telescopes are used as described below, stereoscopic vision may be possible with little or no taper in optical passage 42 or first passage 30.

FIG. 3 illustrates a further embodiment of visualization system 20, wherein a lens means 52 is mounted within first passage 30 of cannula 22. Lens means 52 may comprise a wide-angle lens system, such as a negative focal length lens, or a variety of other lens types, including a simple translucent, non-refractive window. In this embodiment, the body cavity may be visualized by looking directly through first passage 30 and lens means 52, without the use of a separate sleeve for mounting the lens as in previous embodiments.

An additional embodiment of the visualization system of the invention is illustrated in FIGS. 4A–4B. In this embodiment, cannula 22 is adapted for use in laparoscopic and other procedures in which the body cavity is filled with a distension fluid such as carbon dioxide. Cannula 22 includes a sealing means 54 mounted in first passage 30, usually near proximal end 26. In an exemplary embodiment, sealing means 54 comprises a diaphragm of a compliant material such as rubber with one or more slits formed in a middle portion thereof. Other configurations of sealing means 54 are also possible, such as a trumpet valve or stopcock. In this way, sleeve 34 (described above), and/or surgical instruments, prostheses, etc., may be introduced through sealing means 54 and first passage 30 into the body cavity without significant leakage of distension fluid.

Figure 5:
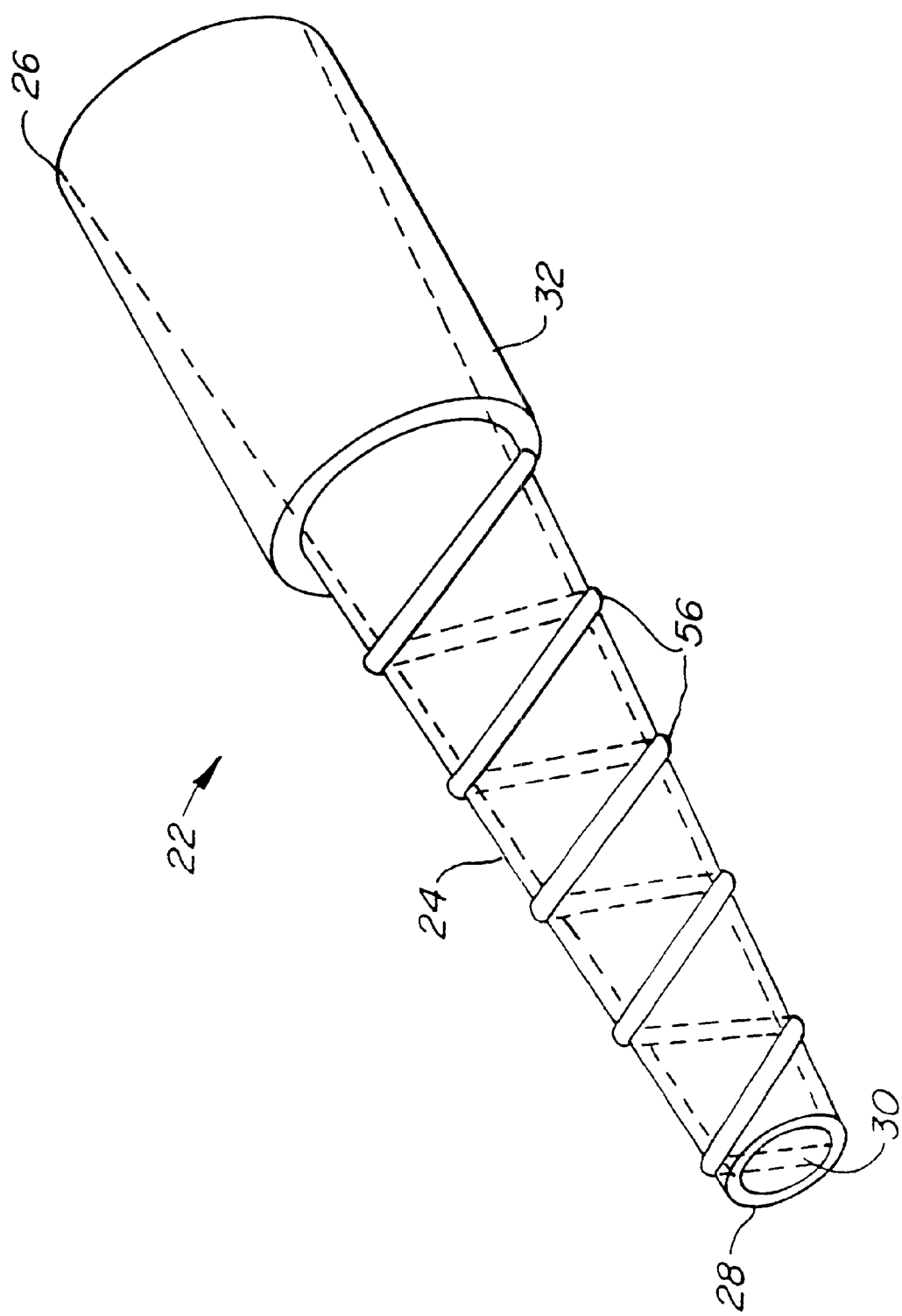
FIG. 5 is a perspective view of a further embodiment of the percutaneous visualization system of the invention.

Cannula 22 may further include retention means for minimizing movement of the cannula when positioned in the wall of a body cavity. In one embodiment, illustrated in FIG. 5, the retention means comprises a plurality of ridges or bumps 56 on the exterior surface of cannula body 24. Ridges 56 are shown in a helical thread pattern, which in some circumstances may assist introduction of the cannula, as well as resisting movement once the cannula is positioned. Alternatively, ridges 56 may be configured in parallel rings or in other patterns which help to increase friction with the tissue and/or bones of the chest, abdomen, or other body cavity.

Figure 6A:
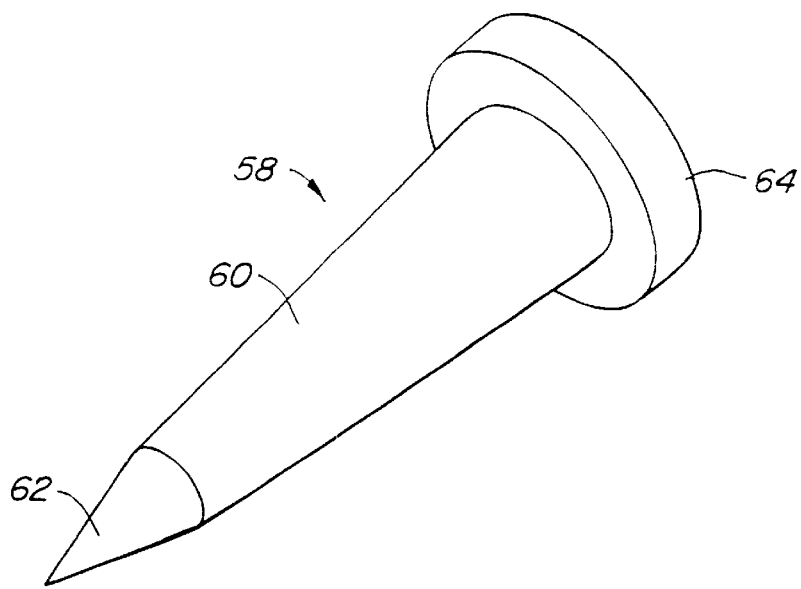
FIG. 6A is a perspective view of an obturator in the visualization system of the invention.
Figure 6B:
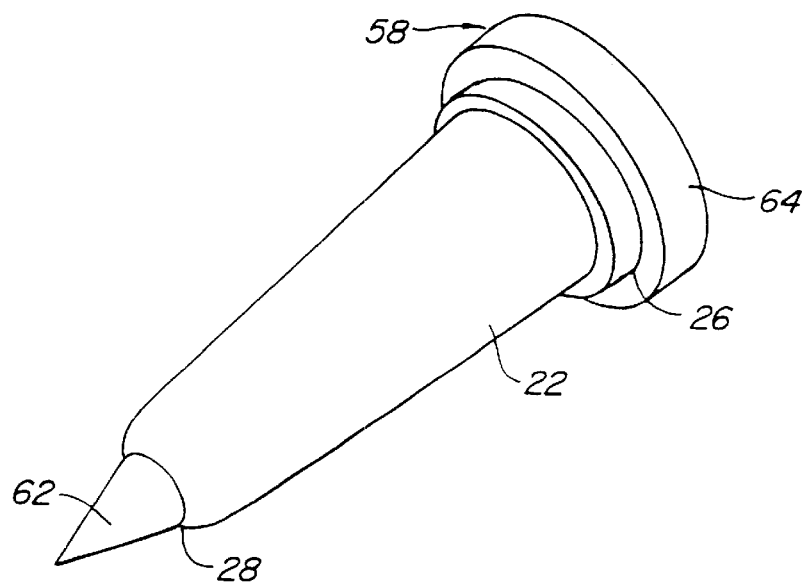
FIG. 6B is a perspective view of the obturator of FIG. 6A positioned within the cannula of the visualization system of the invention.
Figure 6C:
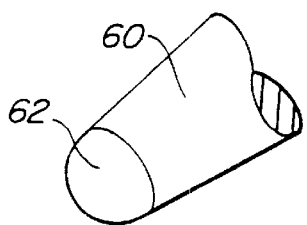
FIG. 6C is a perspective view of a distal portion of an obturator in the visualization system of the invention in an alternative embodiment thereof.
Figure 7:
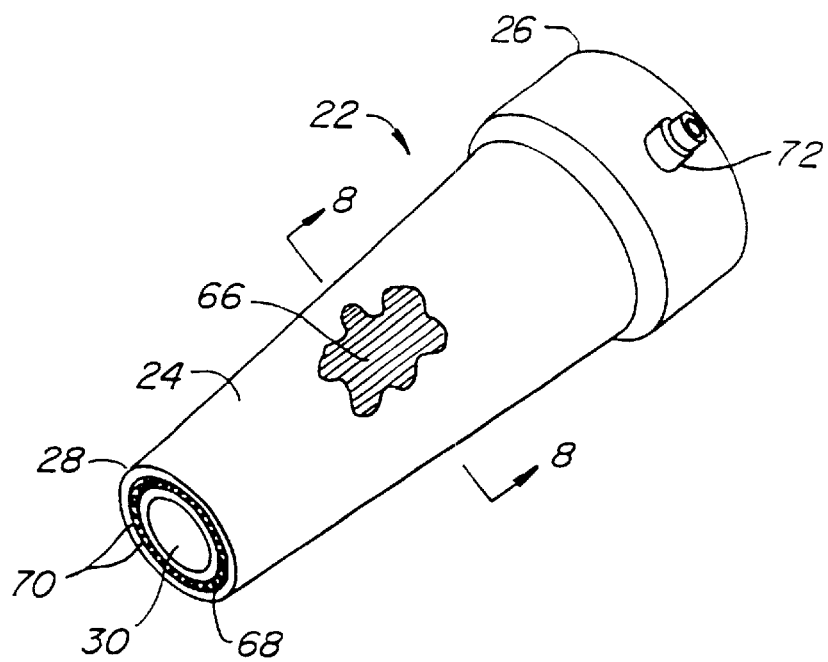
FIG. 7 is a perspective view of a further embodiment of the visualization system of the invention, in which an illumination means is mounted to the cannula.
Figure 8:
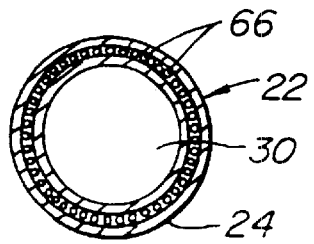
FIG. 8 is a transverse cross-section taken through line 8—8 in FIG. 7.

In a further embodiment, the visualization system of the invention includes, as shown in FIGS. 6A–6C, an obturator 58 to facilitate introduction of cannula 22 into a body cavity. As illustrated in FIG. 6A, obturator 58 comprises a middle section 60, a distal tip section 62, and a proximal end section 64. In a preferred embodiment, at least a portion of middle section 60 is tapered at an angle corresponding to the taper angle of first passage 30 so that obturator 38 nests within cannula 22 with distal tip section 62 exposed distally of the cannula, as shown in FIG. 6B. Preferably, distal tip section 62 tapers to a point to facilitate penetration of tissue. Alternatively, distal tip section 62 may be rounded as shown in FIG. 6C, providing a blunt distal end to reduce trauma as obturator 58 and cannula 22 are urged through a small incision into a body cavity. Obturator 58 may also have a length short enough to prevent damaging the interior organs upon insertion.

FIGS. 7, 8, and 9A–9C illustrate additional embodiments of the invention, wherein cannula 22 includes means for illuminating the body cavity. In an exemplary embodiment, illustrated in FIGS. 7 and 8, the illuminating means comprises a plurality of optical fibers 66 extending longitudinally through a concentric passage 68 in cannula body 24 or embedded in the wall of cannula body 24. Concentric passage 68 is open at distal end 28 of cannula body 24, exposing distal ends 70 of optical fibers 66. Optical fibers 66 are bundled together and coupled at their proximal ends to an optical connector 72 which may be connected to a light source. In this way, light may be transmitted into the body cavity through optical fibers 66. In other embodiments, optical fibers 66 may be disposed in a crescent-shaped lumen 74 as in FIG. 9A, or in one or more non-concentric lumens 76 extending parallel to first passage 30 as in FIG. 9B.

Figure 9A:
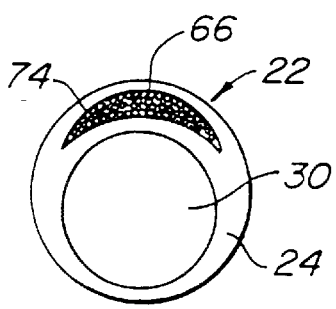
FIGS. 9A–9C are bottom end views of the cannula of the visualization system of the invention, showing alternative configurations of the illumination means.
Figure 9B:
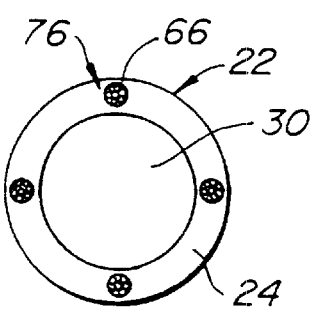
Figure 9C:
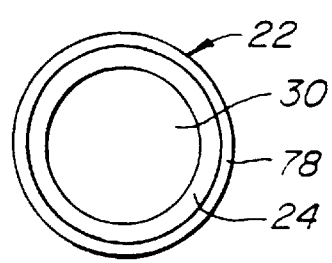

In a further alternative embodiment, shown in FIG. 9C, cannula body 24 is constructed of a light transmitting material such as acrylic or polystyrene. A light source may be positioned near or attached to proximal end 26 of cannula 22 in order to transmit light through distal end 28 of cannula body 24 into the body cavity. Preferably, a sleeve 78 is disposed about the exterior of cannula body 24 to assist light transmission. Sleeve 78 may have a reflective coating on its inner surface adjacent cannula body 24 to reflect light toward distal end 28, or may be of a different index of refraction, so that the sleeve acts as a single optical fiber.

Figure 10:
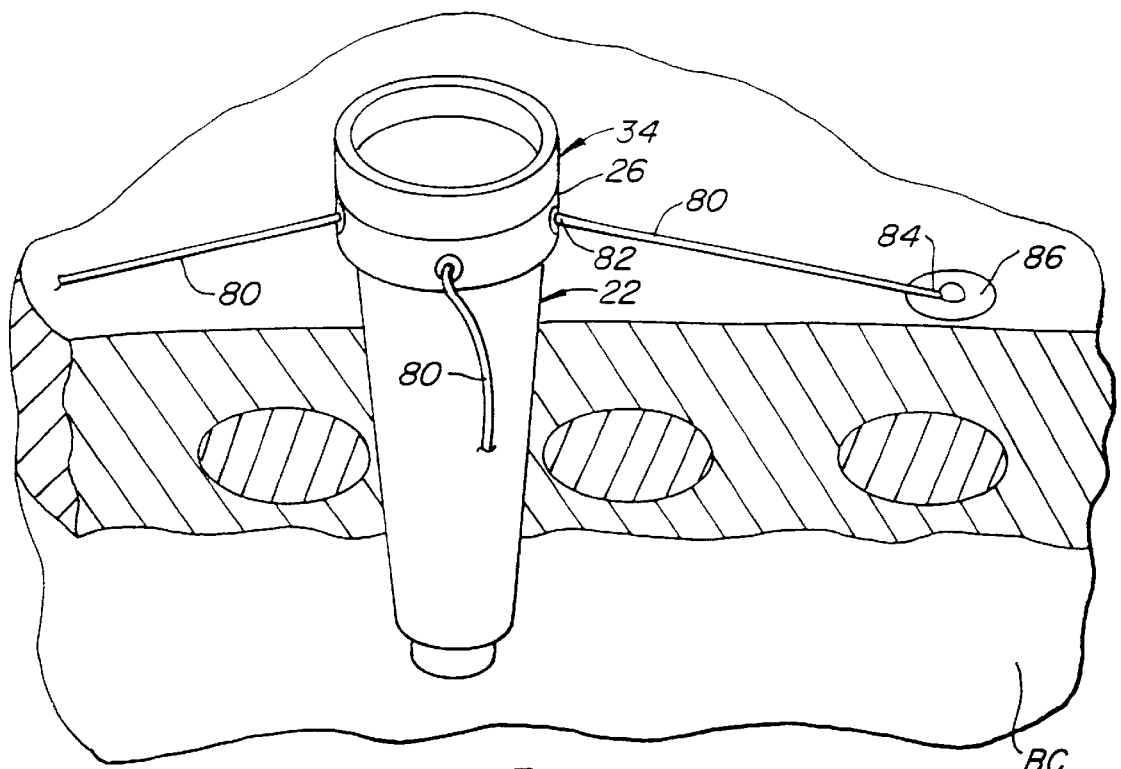
FIG. 10 is a perspective view of the visualization system of the invention positioned in the chest wall of a patient, showing a first embodiment of means for maintaining the position of the cannula relative to the patient's body.

The visualization system of the invention may further include means for maintaining the orientation or position of cannula 22. As illustrated in FIG. 10, in a first embodiment, the means for maintaining the position of the cannula comprises one or more stays 80 which are attached at one end 82 to cannula 22, usually near proximal end 26. Stays 80 may be either a flexible material such as suture, cord, wire, or cable, or a more rigid material such as steel rod. Stays 80 have a free end 84 which may be secured to another structure so as to hold cannula 22 in a particular angular orientation relative to body cavity BC. In one embodiment, free ends 84 are taped or sutured to the patient's skin. An attachment pad 86 may be fixed to each free end 84 for adhesive or suture attachment to the skin. In other embodiments, free ends 84 may be clipped, tied, or otherwise attached to the surgical drapes or to a support structure attached to the operating table (not shown), so as to maintain cannula 22 at a particular angle.

Figure 11:
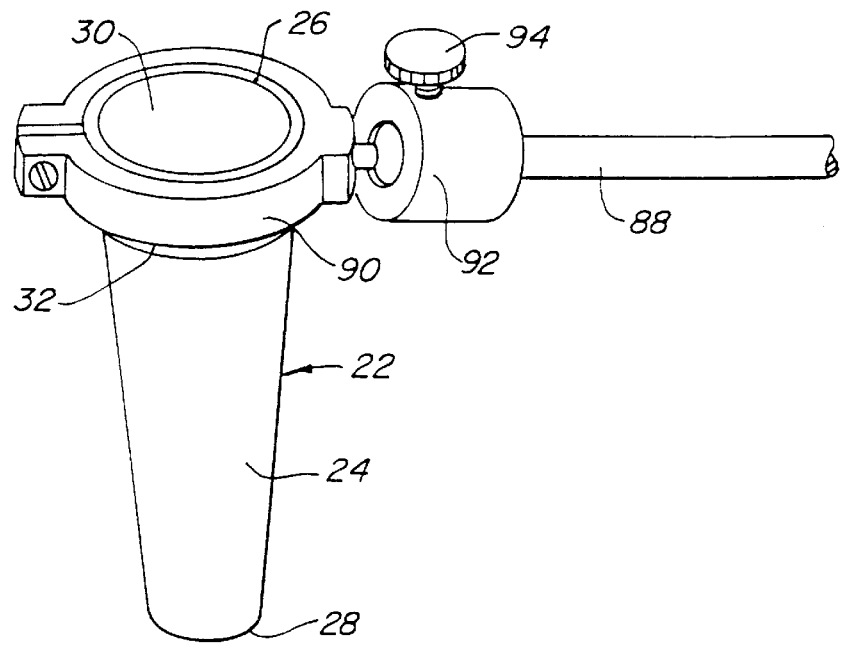
FIG. 11 is a perspective view of the visualization system of the invention showing a further embodiment of the means for maintaining the position of the cannula.

In a second exemplary embodiment, illustrated in FIG. 11, the means for maintaining the position of cannula 22 comprises a rigid or semi-rigid support member 88 which may be fixed to the operating table or other supporting structure. Means are provided for adjustably attaching cannula 22 to support member 88. In one embodiment, cannula 22 is attached to support member 88 by means of a collar 90 which clamps about the cannula body 24 near its proximal end 26, preferably about rim 32. Collar 90 is pivotally attached to support member 88 by a ball-and-socket joint 92, which may be locked in a particular position by means of a set screw 94. In this way, cannula 22 may be positioned in the body cavity and manipulated to a desired angular orientation so that the surgical site is visible through first passage 30. Ball-and-socket joint 92 is then locked by tightening set screw 94, thereby maintaining cannula 22 in the desired position and freeing the user's hands to perform a surgical procedure. Other mechanisms for holding and aligning surgical retractors and scopes may be adapted for this purpose, such as those described in U.S. Pat. No. 5,210,742, the disclosure of which is incorporated herein by reference.

Figure 12:
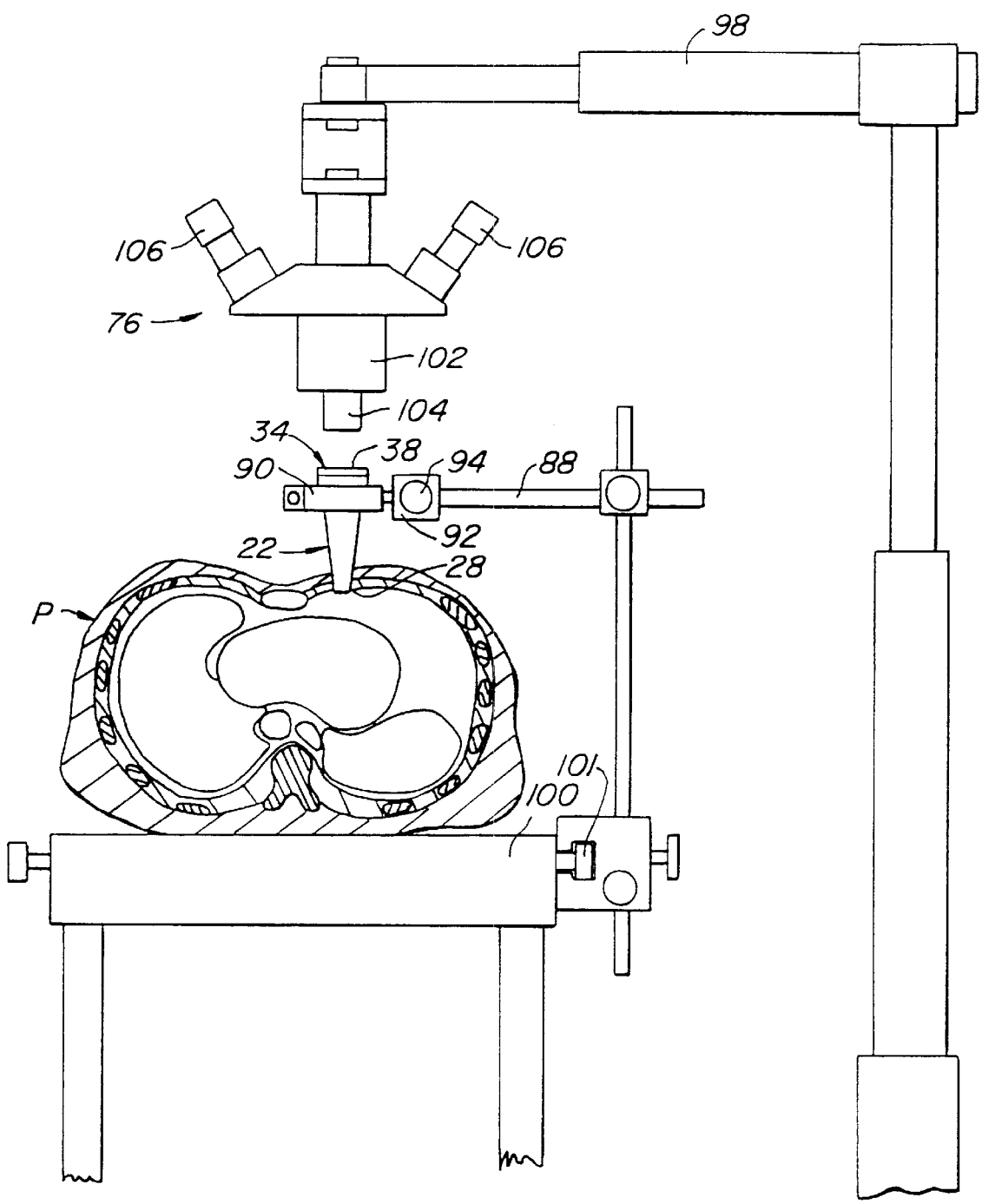
FIG. 12 is a front view of the visualization system of the invention mounted to a surgical operating table on which a patient is shown in cross-section, including a stereo-microscope supported by a floor stand.

FIG. 12 illustrates a visualization system according to the invention which includes magnification means aligned with first passage 30 of cannula 22 and/or optical passage 42 of sleeve 34. In a preferred embodiment, the magnification means comprises a stereo-microscope 96 suspended from a movable arm 98, which may be either floor standing as shown, or ceiling-mounted over operating table 100 on which patient P is positioned. Cannula 22 is positioned such that its distal end 28 is within a body cavity of patient P, such as the thoracic cavity. Cannula 22 is supported by collar 90 coupled to support arm 88, which is mounted to rails 101 on operating table 100. Sleeve 34 is positioned within cannula 22 so that its distal end 40 is within the body cavity.

Stereo-microscope 96 includes a main housing 102 and an objective lens housing 104, which is aligned with optical passage 42 (FIG. 2) at the proximal end 38 of sleeve 34. At least one, and preferably a plurality, of binocular eyepieces 106 are mounted to housing 102, usually in a manner to allow adjustment of eyepiece height, angular disposition, and inter-eyepiece distance. Housing 102 is preferably mounted to arm 98 so as to allow rotation of stereo-microscope 96 about one or more axes.

Figure 13:
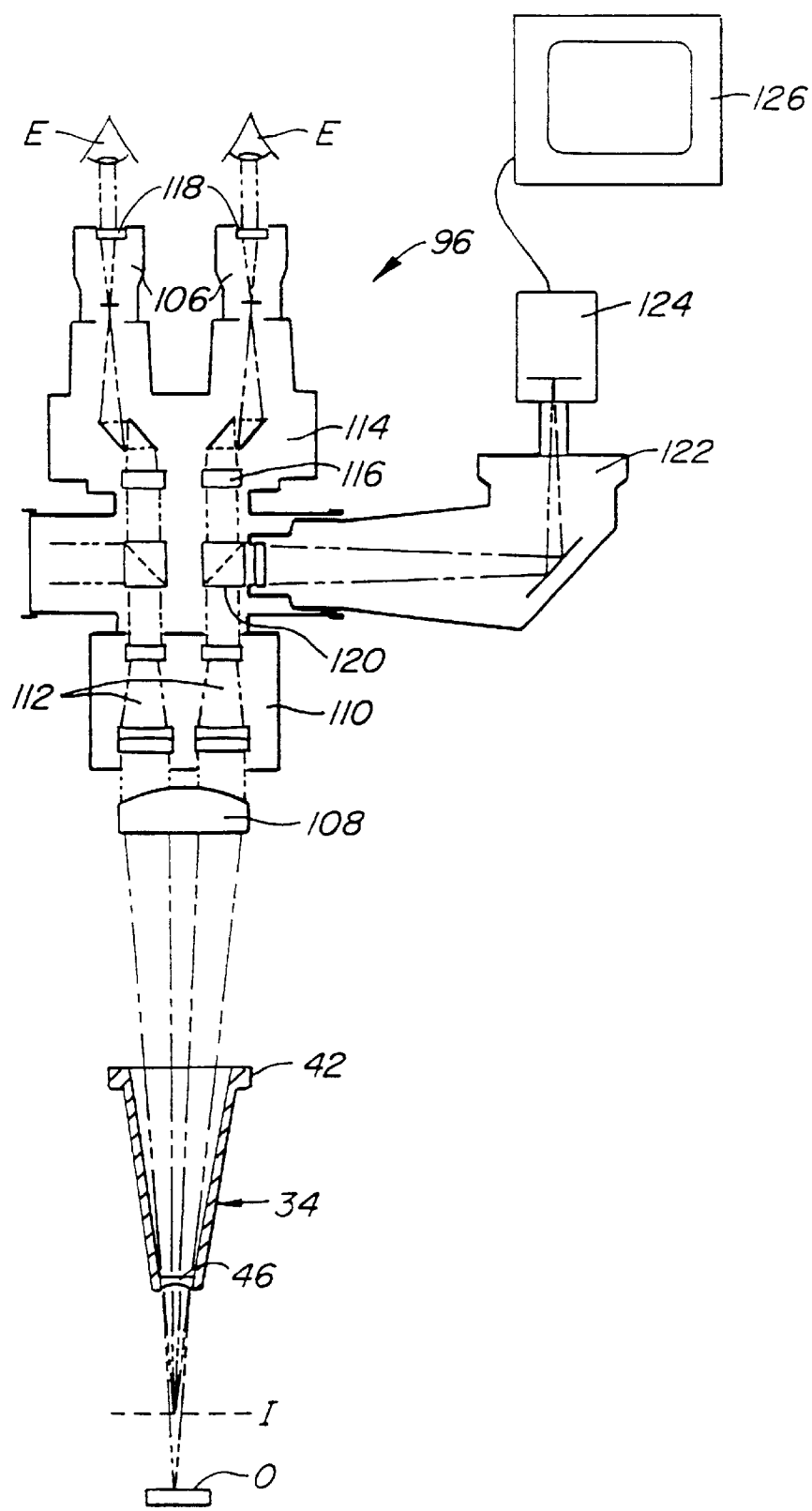
FIG. 13 is a schematic illustration of the stereo-microscope in the visualization system of FIG. 12.

FIG. 13 is a schematic illustration of stereo-microscope 96 in conjunction with sleeve 34 of the present invention. In one exemplary embodiment, stereo-microscope 96 comprises an operating microscope such as the OPMI 7 PH available from Carl Zeiss, Inc., of New York, N.Y., which is described in detail in Hoerenz, "The Operating Microscope," *Journal of Microsurgery* 1:364–369; 1:419–427; 2:22–26, 2:126–139; 2:179–182 (1980), the complete disclosure of which is incorporated herein by reference. Stereo-microscope 96 comprises an objective lens 108 which is optically aligned with optical passage 42 in sleeve 34. Sleeve 34 is equipped with a wide-angle lens 46 mounted in optical passage 42, which receives light rays reflected from an object in plane O in the patient's body cavity. Wide angle lens 46 creates an image of the object on image plane I between lens 46 and the object plane. The height of objective lens 108 is adjusted so that image plane I is situated in the focal plane of objective lens 108. Light rays transmitted from wide-angle lens 46 through optical passage 42 are received by objective lens 108 and transmitted in parallel into magnification section 110. A pair of miniature telescope systems 112 are disposed in magnification section 110 and are configured to allow user adjustment of image magnification. Telescope systems 112 take the parallel ray image from objective lens 108 and increase or decrease its magnification (as adjusted by the user). The light rays leave magnification section 110 in parallel and are transmitted into a binocular tube 114. Binocular tube 114 includes a pair of objective lenses 116 which magnify the image of object O and transmit it to a pair of ocular lenses 118 in eyepieces 106, which may be aligned with each of the user's eyes E. In an exemplary configuration, with a 300 mm objective lens 108 and 125 mm binocular tube 114, the magnification may be varied between 3.3 (for a field of view of 60 mm diameter) and 20.8 (for a field of view of 10 mm diameter).

Stereo-microscope 96 may further include one or more beam splitters 120 disposed between magnification section 110 and binocular tube 114. Beam splitter 120 allows a portion of the light rays from object O to be reflected to additional eyepieces 106 (see FIG. 12), and/or to a camera mount 122 to which a video camera 124 may be mounted. In this way, multiple observers may simultaneously view a procedure either by looking through eyepieces 106 or by viewing a video monitor 126 connected to video camera 124.

In an alternative embodiment (not illustrated), a single, large magnifying lens configured to be looked through with both of the user's eyes, similar to the lenses used, for example, in photographic slide viewers, is mounted to proximal end 26 of cannula body 24, or positioned in optical alignment with first passage 30 separated from cannula 22. In this way, stereoscopic magnification of the surgical site is accomplished without requiring the user to align his or her eyes with the binocular eyepieces of a microscope, and further allowing multiple observers to look through cannula 22 simultaneously.

Figure 14:
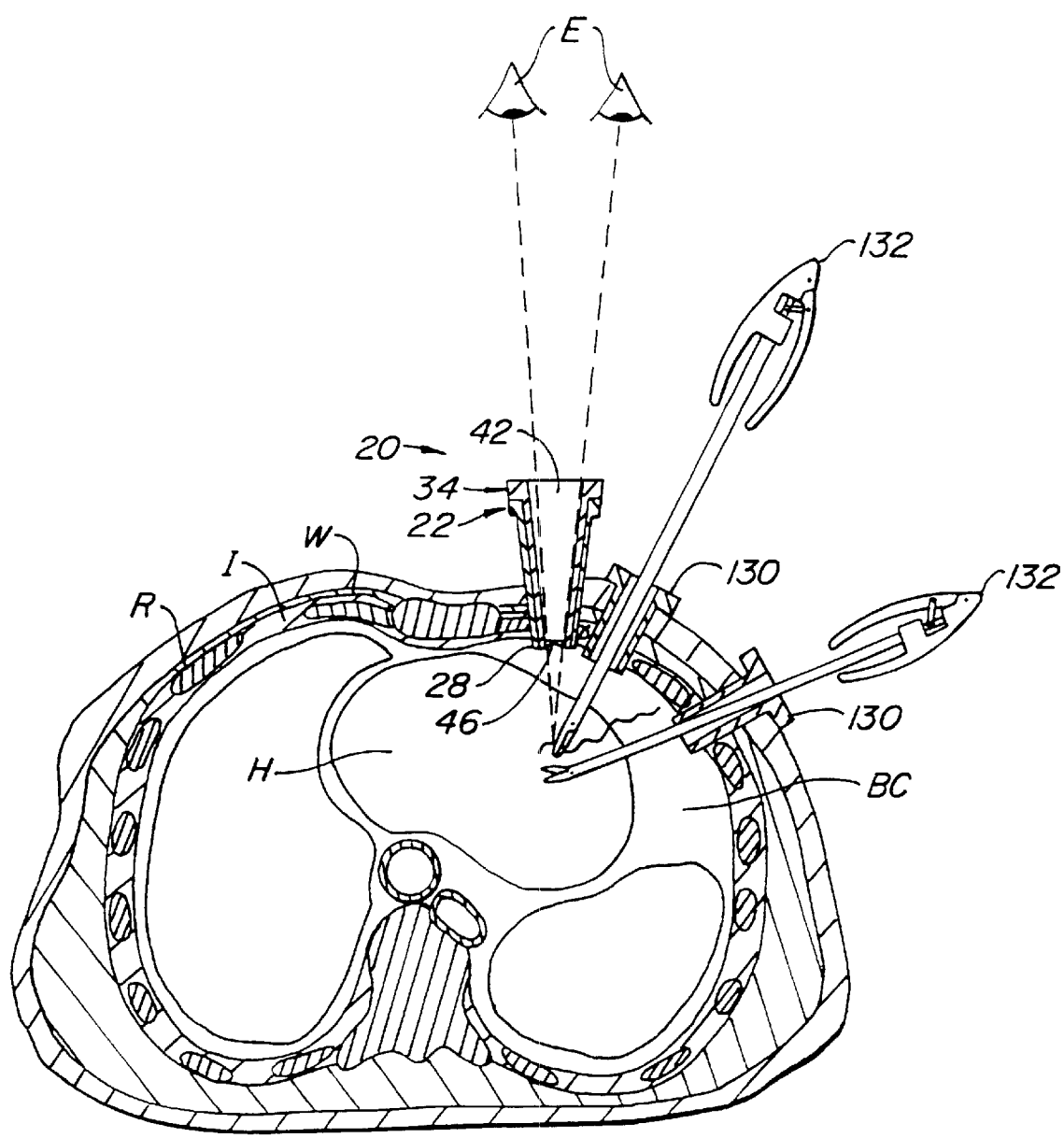
FIG. 14 is a front cross-sectional view of the visualization system of the invention positioned in a body cavity of a patient, illustrating the performance of a minimally-invasive surgical procedure.

FIG. 14 illustrates the visualization system of the present invention positioned in a body cavity BC of a patient. In the figure, body cavity BC represents the thoracic cavity, but it should be understood that the invention will be useful for visualization of procedures in various body cavities, including the abdomen and pelvis. Body cavity BC is enclosed by a wall W, in which are disposed a plurality of ribs R of the patient's rib cage. Ribs R are separated by intercostal spaces I, which typically range in width from about 5 mm to 20 mm in adult patients. The patient's heart H is disposed within body cavity BC, usually about 2 cm to 6 cm below the interior surface of wall W.

Cannula 22 is positioned in an intercostal space I between a pair of ribs R so that the distal end 28 of cannula 22 is within body cavity BC. Usually, an obturator (not shown in FIG. 14) is positioned in first passage 30 of cannula 22 to facilitate penetration of wall W during introduction, as described above in connection with FIGS. 6A–6C. Sleeve 34 is positioned in cannula 22 so that wide-angle lens 46 is disposed within body cavity BC. Cannula 22 may be manipulated to a desired angular orientation and depth, and secured in position by means of stays or a clamp, as described above with reference to FIGS. 10 and 11. In addition, illuminating means, either integral with cannula 22 or on an independent device introduced through a separate incision or cannula (not shown in FIG. 14), may be utilized to transmit light into the body cavity.

Additional trocar sleeves 130 of well-known construction are positioned in intercostal spaces I between adjacent ribs R to facilitate introduction of surgical instruments to perform a procedure in body cavity BC. A variety of minimally-invasive procedures may be performed, including those described in co-pending application Ser. No. 08/023,778, which has been incorporated herein by reference. The invention is particularly well-adapted for visualization of microsurgical procedures such as thoracoscopic CABG, due to the invention's extremely high image quality, its wide-angle and magnification capabilities, and its facilitation of direct visualization of the surgical site. For the performance of CABG, surgical instruments 132, which may comprise forceps, scissors, needle drivers, graspers, and other specially-designed instruments, are introduced through one or more trocar sleeves 130 into body cavity BC to create an arterial blood source, and to perform an anastomosis between the arterial blood source and a coronary artery on heart H.

Using the visualization system of the invention, the surgeon may directly and stereoscopically visualize the procedure through optical passage 42 in sleeve 34. Wide-angle lens 46 allows the surgeon to see a larger area in the body cavity, if desired. Sleeve 34 together with wide-angle lens 46 may be removed to substitute a different lens size or type, or the sleeve may be left out of cannula 22 to allow direct viewing with no lens. In addition, surgical instruments may be introduced through cannula 22 to assist in the procedure. Visualization may be enhanced by the use of multiple cannulas positioned in various locations in the chest wall, as well as by using conventional endoscopic visualization devices such as thoracoscopes positioned through trocar sleeve 130. Magnification means, such as the stereo-microscope illustrated in FIGS. 12–13, may be positioned in alignment with optical passage 42 to magnify the image. Preferably, a stereo-microscope having multiple binocular eyepieces is utilized, to allow a plurality of observers to view the procedure simultaneously. Alternatively, the surgeon may wear surgical loupes (magnifying eyeglasses) to magnify the image viewed through optical passage 42.

Figure 15:
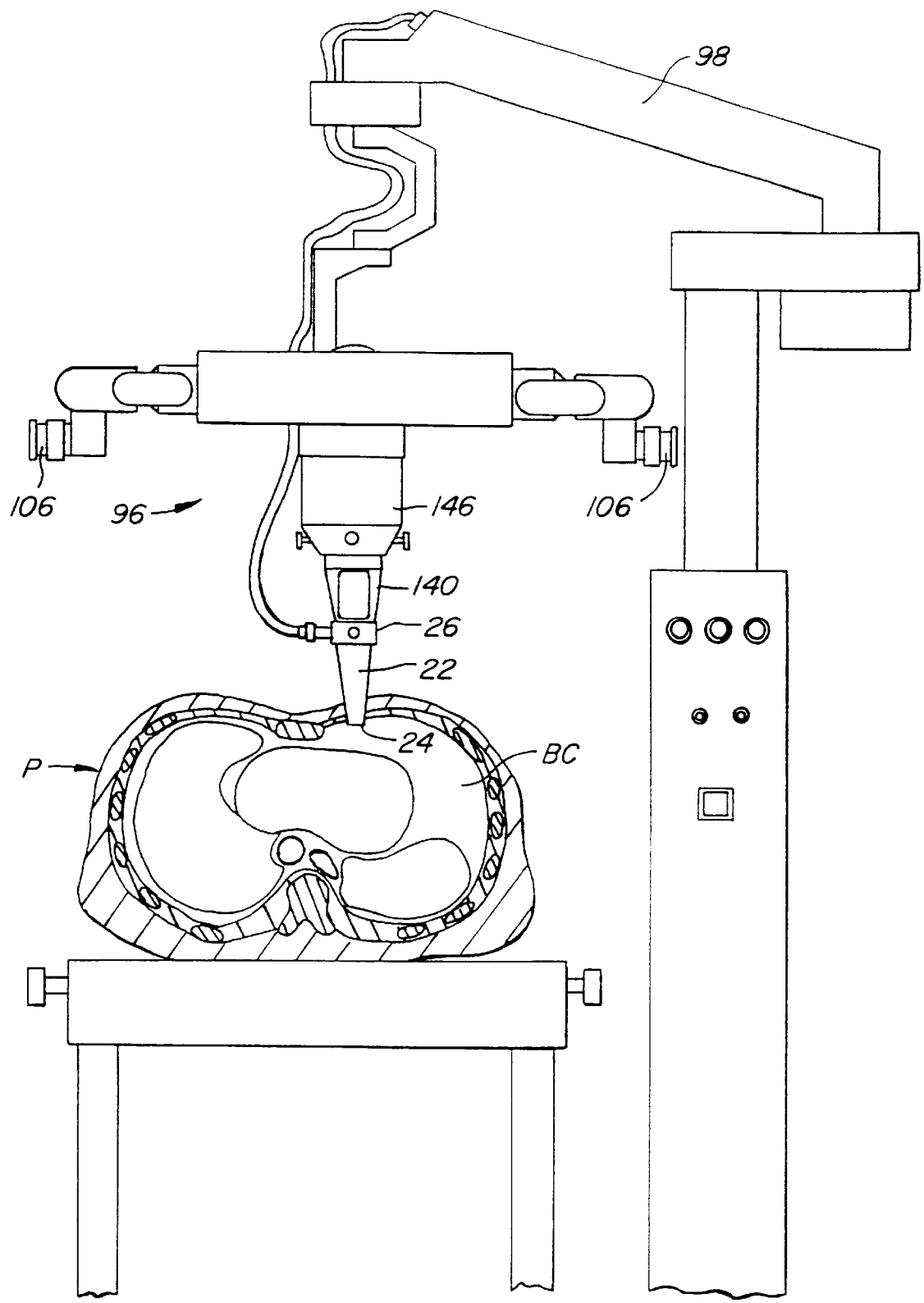
FIG. 15 is a front view a further embodiment of a visualization system according to the invention positioned in a patient's body, shown in cross-section.
Figure 16:
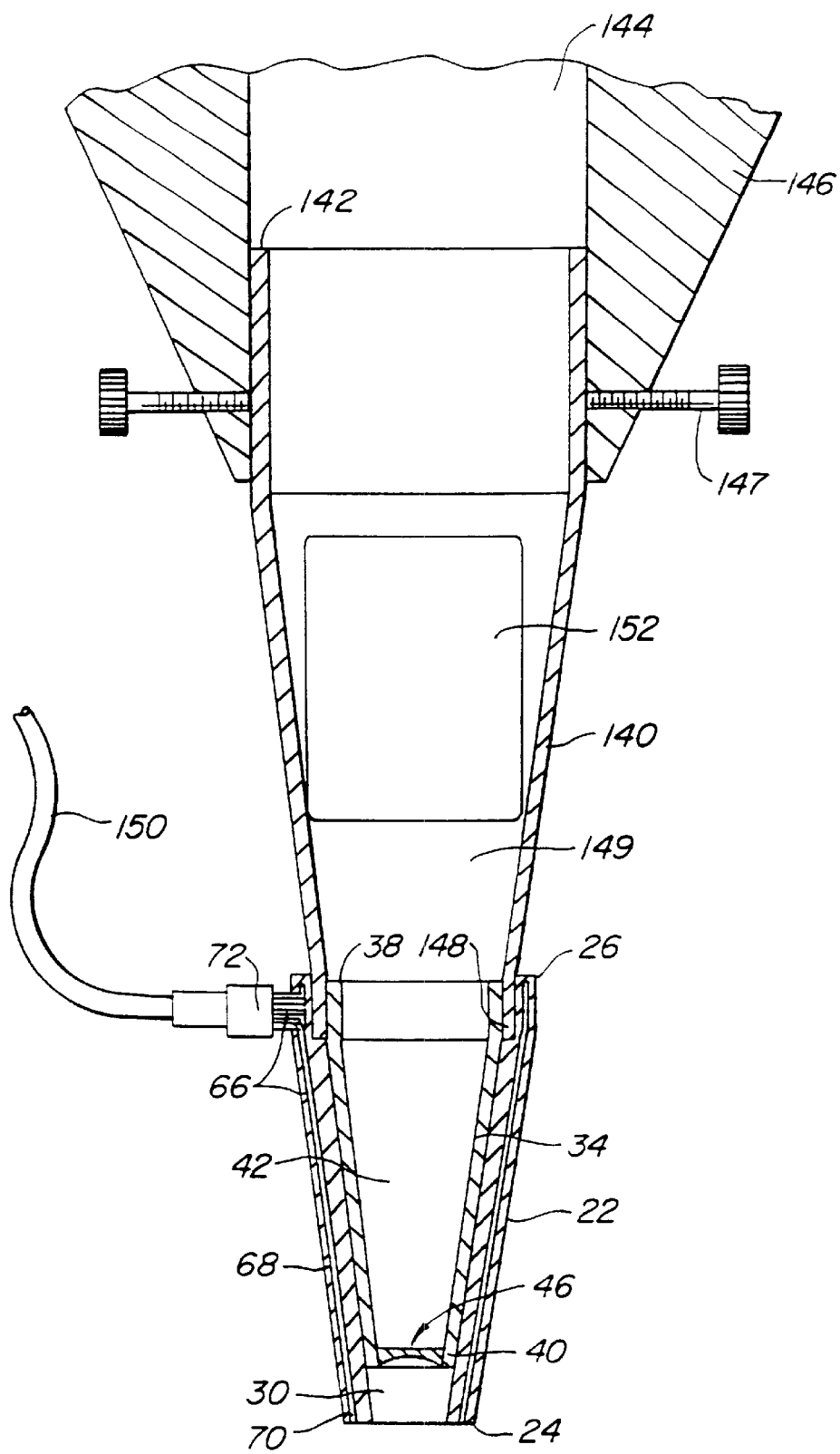
FIG. 16 is a front cross-sectional view of a coupling sleeve and cannula in the visualization system of FIG. 15.

Still another embodiment of the visualization system of the invention is illustrated in FIGS. 15–16. In this embodiment, as shown in FIG. 15, cannula 22 is mechanically coupled to stereomicroscope 96 by a coupling sleeve 140. In this way, first passage 30 of cannula 22 is maintained in optical alignment with the objective lens of stereomicroscope 96, and cannula 22 is supported and maintained in a desired orientation by stereomicroscope 96, eliminating the need for a separate support structure, stays, or clamps.

In this embodiment, stereomicroscope 96 is preferably one which is not only linearly positionable along three perpendicular axes, but is rotationally positionable about at least two axes to allow the objective lens of the microscope to be aligned with cannula 22 in a variety of angular orientations relative to body cavity BC. For example, the OPMI MD series or OPMI CS-I surgical microscopes available from Carl Zeiss, Inc. of Thornwood, N.Y., may be utilized.

A more detailed illustration of cannula 22 and coupling sleeve 140 of the system of FIG. 15 is seen in FIG. 16. As described above, cannula 22 has a first passage 30 in which a sleeve 34 may be positioned. A lens 46, usually comprising a wide-angle lens system or negative focal length lens, is mounted near the distal end 40 of sleeve 34. Optical fibers 66 extend from optical connector 72 through a concentric lumen 68 in cannula 22, such that light is transmitted through their distal ends 70 to illuminate the body cavity. Optical connector 72 is connected to an optical cable 150 which is connected to a light source.

Coupling sleeve 140 has a proximal end 142 disposed within a cylindrical bore 144 in an adaptor assembly 146 attached to stereomicroscope 96. Preferably, coupling sleeve 140 is slidable within bore 144 to allow adjustment of the position of coupling sleeve 140 relative to microscope 96 along its optical axis, so that lens 46 may be optimally positioned according to the focal length of the microscope's objective lens. Various other types of mechanisms may be used to facilitate positional adjustment of coupling sleeve 140, including a rack and pinion or helical threads on coupling sleeve 140. Set screws 147 engage coupling sleeve 140 to hold it in position. An axial passage 149 extends between proximal end 142 and distal end 148.

Distal end 148 of coupling sleeve 140 is attached to proximal end 26 of cannula 22 by set screws, adhesive bond, band clamp, or other known means. In one embodiment, cannula 22 is attached to coupling sleeve 140 such that it may be easily decoupled therefrom to allow cannula 22 to be independently introduced into the body cavity and oriented by direct vision through optical passage 42, after which microscope 96 may be aligned with cannula 22 and coupling sleeve 140 reattached to the cannula. The ability to quickly decouple cannula 22 from coupling sleeve 140 also allows cannula 22 to be removed from microscope 96 after use for disposal or sterilization.

To facilitate interchanging sleeves 42 having various types of lenses 46, a window 152 is disposed on a lateral side of coupling sleeve 140. In this way, sleeve 34 may be grasped near its proximal end 38 by reaching one or more fingers through window 152. Sleeve 34 may thus be removed from first passage 30 for replacement with an alternate sleeve having a different type of lens, or, if visualization is compromised by debris or humidity, for replacement with a clean or defogged lens.

In use, cannula 22 is first decoupled from stereomicroscope 96 and positioned at the desired location on patient P. Cannula 22 is percutaneously introduced through a small incision or puncture so that its distal end 28 is within body cavity BC. The angular orientation of cannula 22 may be adjusted by looking directly through optical passage 34 to observe the contents of body cavity BC and by manipulating cannula 22 until the desired site in body cavity BC is aligned with optical passage 34. Stereomicroscope 96 is then positioned so that its objective lens is optically aligned with optical passage 34, and coupling sleeve 140 is attached to the proximal end 26 of cannula 22. Further positional adjustment may be accomplished by manipulating stereomicroscope 96 while cannula 22 remains coupled to coupling sleeve 140.

Cannula 22 and sleeve 34 in the embodiments described above may be made of any of a variety of biocompatible materials. However, because these components may penetrate into a body cavity and come into contact with living tissue, they must be sterile. Therefore, cannula 22 and sleeve 34 are preferably constructed of a material which may be sterilized between uses, or which is disposable after each use. Sterilizable materials suitable for cannula 22 and/or sleeve 34 include stainless steel, anodized aluminum, and other biocompatible metals. Materials which have the necessary performance characteristics yet which are of sufficiently low cost to be disposable include plastics such as polycarbonate, acetonitrile butyl styrene (ABS), or polyvinyl chloride (PVC).

Figure 17:
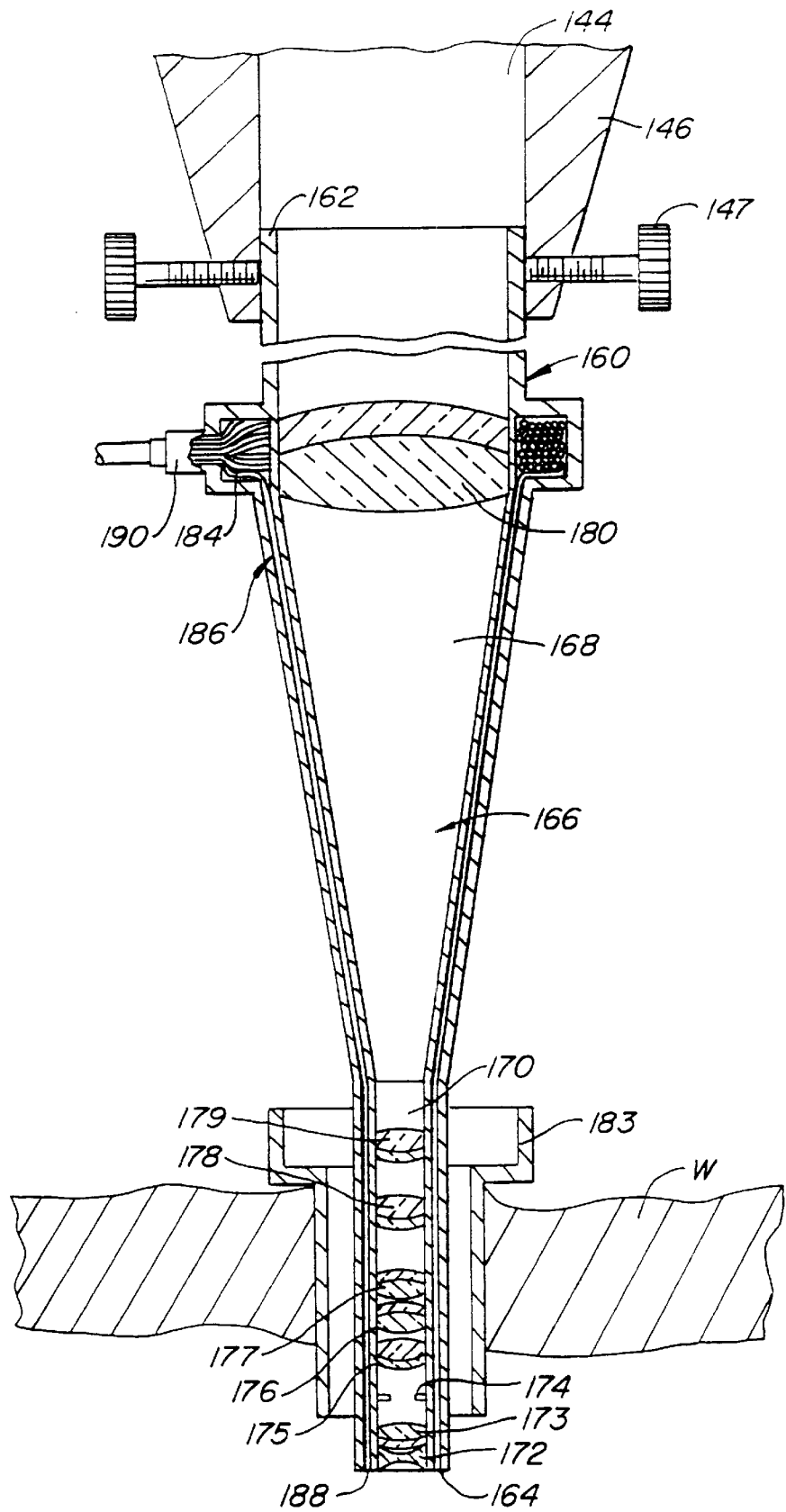
FIG. 17 is a front cross-sectional view of a cannula coupled to a microscope in a further embodiment of a visualization system according to the invention.

Yet another embodiment of the visualization system of the invention is illustrated in FIG. 17. In this embodiment, an adaptor assembly 146 is mounted to a stereomicroscope in the manner described above in connection with FIGS. 15–16. A tubular cannula 160 has a proximal end 162 slidably disposed within passage 144 and held by set screws 147. Cannula 160 has a distal end 164 configured for percutaneous introduction into a body cavity through a body wall W, usually having a maximum width or diameter which is less than about 20 mm, preferably about 5 mm–10 mm, so as to pass through an intercostal space of the rib cage. An optical passage 166 extends between proximal end 162 and distal end 164, having a tapered proximal section 168 and a non-tapered distal section 170.

In a preferred embodiment, a lens system is mounted within optical passage 166 to facilitate visualization of a field within the body cavity which is significantly larger than the transverse cross-sectional area of cannula 160 at distal end 164. In an exemplary configuration, a double concave negative focal length lens 172 is disposed in distal section 170 of optical passage 166 near distal end 164. A first achromat 173 is mounted proximally of lens 172, and an aperture or iris 174 is disposed proximally of achromat 173. Second, third, fourth, fifth, and sixth achromats 175, 176, 177, 178, 179 are disposed serially within distal section 170 proximal to iris 174. A larger achromat 180 is mounted within optical passage 166 near the proximal end of proximal section 168.

Preferably, cannula 160 and the lens system within optical passage 166 is configured to pass through a trocar sleeve 183 having an inner diameter of 12 mm or smaller (113 mm$^2$ transverse cross-sectional area) while providing a field of view of between 5° and 90°, preferably about 20°–60°, off of the optical axis defined by optical passage 166. This will allow visualization of a field within the body cavity of at least about 30 mm diameter (707 mm$^2$ area), and preferably about 50–60 mm diameter (1963 mm$^2$–2827 mm$^2$ area), at a distance of between 20 mm and 80 mm, preferably around 30 mm to 60 mm, from distal end 164. In addition, the lens system should provide an image situated at the focal length of the microscope's objective lens which is within the field of view of a conventional surgical microscope. For example, a conventional surgical microscope with 5–25× magnification and a 175 mm objective lens may have a field of view between 6 mm and 28 mm in diameter (depending upon magnification).

Although a variety of lens combinations are possible in cannula 160, in an exemplary embodiment, double concave lens 172 has a focal length of −6 mm, achromats 173, 177 each have a focal length of 35 mm, achromats 175, 176, 178, 179 have a focal length of 12.5 mm, and achromat 180 has a focal length of 150 mm. All of the lenses in distal section 170 of optical passage 166 have a diameter of 6.25 mm, while achromat 180 has a diameter of 30 mm. Iris 174 may have various radii depending upon the depth of field desired, as is usually between about 0.50 mm and 1.25 mm, for a working F number between 56 and 22. Achromats 173, 175, 176, 177, 178, 179, 180 are of conventional construction, consisting of two optical components of different densities bonded together so as to correct chromatic aberrations that can occur from the diffraction effects of a lens of a single type of glass. Such achromats are available from, for example, Edmund Scientific Co. of Barrington, N.J.

Figure 17A:
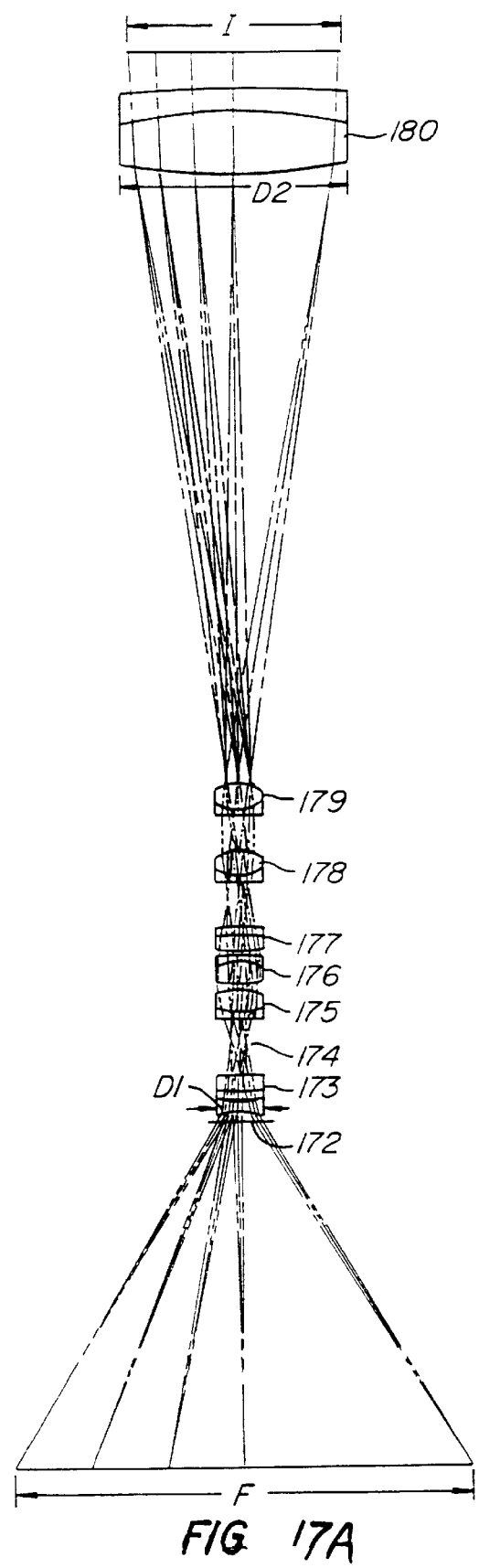
FIG. 17A is a schematic illustration of the light path through the cannula of FIG. 17.

The light path resulting from the foregoing lens system is illustrated in FIG. 17A. For lenses 172–179 of diameter D1 of 6.25 mm, and achromat 180 of diameter D2 of 30 mm, a field of diameter F up to about 60 mm is visible, and an image of diameter I of about 28 mm is provided for viewing by the microscope at the focal length of its objective lens. This image is then magnified by, e.g., 5×–25× by the microscope objective, and split into separate paths for stereoscopic viewing by means of a binocular eyepiece (see FIGS. 13 and 15).

In this way, cannula 160 may be non-tapered, may have a smaller diameter, and may have a greater length than previous embodiments while still providing stereoscopic wide-angle visualization into the body cavity through a small percutaneous penetration. Conveniently, cannula 160 may be percutaneously introduced directly into the body cavity through a small incision or puncture, or through a standard trocar sleeve or other access cannula 183, which may be a Thoracoport™ available from United States Surgical Corporation of Norwalk, Conn.

Cannula 160 is further provided with means for illuminating the body cavity, which may comprise a plurality of optical fibers 184 disposed in an annular passage 186 so that light is transmitted through their distal ends 188 into the body cavity. Optical fibers 184 are connected to an optical connector 190 for connection to a light source. Alternatively, all or a portion of cannula 160 may be constructed of a light conductive material such as acrylic to form a light pipe to transmit light into the body cavity.

It will be understood to those of skill in the art that, as an alternative to mounting cannula 160 to a conventional surgical microscope, the lens system of cannula 160 along with the objective lens, telescope systems, eyepieces and other optics of the microscope may be mounted into a single body or frame to create an integrated device which is more compact and portable.

In an alternative embodiment, a distal portion of cannula 160 may be configured to allow viewing from an angle of, e.g., 45°–90° relative to the axial direction as defined by the proximal portion of optical passage 166 to facilitate viewing portions of the body cavity lateral to the puncture through which cannula 160 is introduced. A reflecting prism may be mounted in optical passage 166 near distal end 164 to reflect light from the distal end 164 toward the proximal portions of optical passage 166. An optical design like that used in commercially-available angled endoscopes such as the Olympus 45° endoscope (Catalog No. A5256) available from Olympus Corp., Medical Instruments Division, Lake Success, N.Y., may be utilized. In another embodiment (not illustrated), cannula 160 has a steerable distal end which may be deflected into a variety of angles within the body cavity by manipulating a steering wire or other actuation mechanism extending from distal end 164 to a location outside of the body cavity.

Figure 18A:
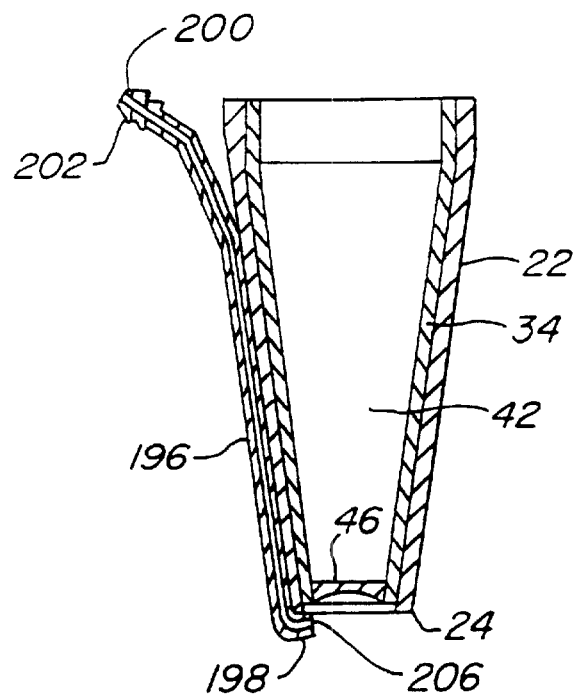
FIGS. 18A–18B are front cross-sectional views of a visualization cannula in an additional embodiment of a visualization system according to the principles of the invention.
Figure 18B:
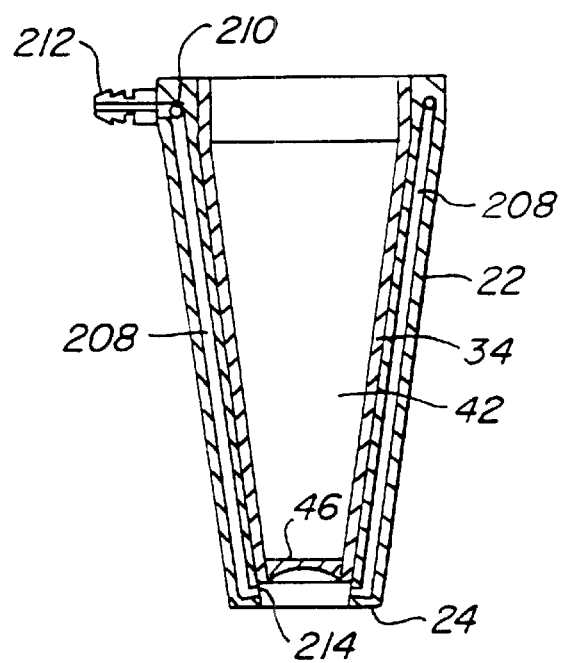

FIGS. 18A–18B illustrate a further embodiment of a visualization system according to the invention, wherein cannula 22 is provided with means for delivering a fluid into the body cavity to enhance visualization. Such fluid delivery may accomplish various purposes, including irrigation of a site to be visualized, removal of debris from lens 46, or dehumidifying or defogging lens 46. In a first embodiment, shown in FIG. 18A, a delivery tube 196 is fixed to the exterior of cannula 22 and has a distal end 198 disposed near distal end 24 of cannula 22, and a proximal end 200 having a hose barb 202 or other connector configured for connection to a fluid delivery source. A lumen 204 extends from proximal end 200 to distal end 198, and is in communication with an opening 206 at distal end 198. In a preferred embodiment, opening 206 is positioned so as to direct a fluid onto the distal surface of lens 46. In this way, a gas such as carbon dioxide or air can be directed toward the surface of the lens to dry the lens surface and keep it free of fog. Alternatively, a liquid such as saline can be delivered to remove debris on lens 46 and/or cannula 22 which may be obstructing vision, or to irrigate a site in the body cavity.

Rather than being fixed to cannula 22, delivery tube 196 may be slidably coupled to cannula 22 to allow delivery tube 196 to be introduced or removed from the body cavity as desired. For example, rings or channels may be provided on the exterior surface of cannula 22 through which delivery tube 196 may be inserted and advanced distally until its distal opening 206 is aligned with lens 46.

FIG. 18B illustrates an alternative configuration wherein one or more fluid delivery lumens 208 are formed in the wall of cannula 22, each fluid delivery lumen 208 being connected by a manifold 210 to a hose barb 212 or other means for connection to a fluid delivery source. Each fluid delivery lumen 208 has an opening 214 at its distal end positioned to direct fluid toward the distal surface of lens 46. A plurality of individual delivery lumens 208 may be arranged circumferentially about cannula 22, or a single concentric delivery lumen 208 may be used with a plurality of openings 214 near distal end 24.

Cannula 22 of FIGS. 18A–18B may further be provided with light transmission means for lighting the body cavity. Cannula 22 may be itself constructed of a light transmitting material such as acrylic or polystyrene, or optical fibers may be mounted to or embedded in the wall of cannula 22 and connected to an external light source to transmit light into the body cavity, as described with reference to FIGS. 7, 8, and 9A–9C above.

While the above is a complete description of the preferred embodiments of the invention, various alternatives, modifications, and equivalents may be used. Therefore, the above description should not be taken as limiting the scope of the invention, which is defined by the appended claims.

What is claimed is:

1. A surgical microscope comprising a microscope body, lens means attached to the microscope body for magnifying an object image, an eyepiece attached to the microscope body for viewing the magnified object image, and coupling means attached to the microscope body for retaining a supplementary lens in optical alignment with the lens means, the coupling means being configured for introducing the supplementary lens through a percutaneous penetration into a body cavity, wherein the coupling means comprises a sleeve having an interior in which the supplementary lens is positioned, the sleeve having an aperture in a side thereof in communication with the interior to facilitate interchanging the supplementary lens with other lenses without decoupling the sleeve from the lens means.

2. A surgical microscope comprising a microscope body, lens means attached to the microscope body for magnifying an object image, an eyepiece attached to the microscope body for viewing the magnified object image, and coupling means attached to the microscope body for retaining a supplementary lens in optical alignment with the lens means, the coupling means being configured for introducing the supplementary lens through a percutaneous penetration into a body cavity and allowing the supplementary lens to be interchanged with an alternate lens without moving the microscope body.

3. A surgical microscope comprising a microscope body, lens means attached to the microscope body for magnifying an object image, an eyepiece attached to the microscope body for viewing the magnified object image, and coupling means attached to the microscope body for retaining a supplementary lens in optical alignment with the lens means, the coupling means comprising a cannula having a passage in which the supplementary lens may be removably positioned, the cannula having a distal end configured for introduction into the body cavity through a percutaneous penetration, the coupling means being configured for introducing the supplementary lens through a percutaneous penetration into a body cavity.

4. The surgical microscope of claim 3 wherein the coupling means further comprises a sleeve disposed within the cannula.

5. The surgical microscope of claim 4 wherein the cannula is configured for positioning within an intercostal space between two adjacent ribs.

6. The surgical microscope of claim 5 wherein the cannula has a transverse width or diameter of less than about 20 mm.

7. A surgical microscope comprising a microscope body, lens means attached to the microscope body for magnifying an object image, an eyepiece attached to the microscope body for viewing the magnified object image, and coupling means attached to the microscope body for retaining a supplementary lens in optical alignment with the lens means, the coupling means being configured for introducing the supplementary lens through a percutaneous penetration into a body cavity, the coupling means comprising a sleeve having an interior in which the supplementary lens is positioned, the sleeve having an aperture in a side thereof in communication with the interior to facilitate interchanging the supplementary lens with at least one other lens without decoupling the sleeve from the lens means.

* * * * *